United States Patent
Gaire et al.

(10) Patent No.: US 12,031,988 B2
(45) Date of Patent: Jul. 9, 2024

(54) DISTANCE-BASED TISSUE STATE DETERMINATION

(71) Applicant: HOFFMANN-LA ROCHE INC., Little Falls, NJ (US)

(72) Inventors: Fabien Gaire, Penzberg (DE); Karin Emilia Andersson, Penzberg (DE); Franziska Braun, Penzberg (DE); Konstanty Korski, Penzberg (DE); Fabian Schmich, Penzberg (DE)

(73) Assignee: Hoffmann-La Roche, Inc., Little Falls, NJ (US)

( * ) Notice: Subject to any disclaimer, the term of this patent is extended or adjusted under 35 U.S.C. 154(b) by 552 days.

(21) Appl. No.: 17/284,610

(22) PCT Filed: Oct. 23, 2019

(86) PCT No.: PCT/EP2019/078819
§ 371 (c)(1),
(2) Date: Apr. 12, 2021

(87) PCT Pub. No.: WO2020/083970
PCT Pub. Date: Apr. 30, 2020

(65) Prior Publication Data
US 2021/0343009 A1 Nov. 4, 2021

(30) Foreign Application Priority Data
Oct. 23, 2018 (EP) .................................... 18202125

(51) Int. Cl.
*G01N 33/574* (2006.01)
*G06T 7/00* (2017.01)

(52) U.S. Cl.
CPC ......... *G01N 33/574* (2013.01); *G06T 7/0012* (2013.01); *G06T 2207/30024* (2013.01)

(58) Field of Classification Search
CPC ................ G01N 33/574; G06T 7/0012; G06T 2207/30024
See application file for complete search history.

(56) References Cited

U.S. PATENT DOCUMENTS

2009/0257640 A1* 10/2009 Gossage ................ G06V 10/50
382/133
2011/0258370 A1* 10/2011 Sharon ................ G11C 16/349
711/E12.008

(Continued)

FOREIGN PATENT DOCUMENTS

WO    WO-2017171720 A1    10/2017
WO    WO-2017/198790 A1   11/2017
WO    WO-2018086985 A1    5/2018

OTHER PUBLICATIONS

European Office Action, dated Sep. 1, 2023, issued in corresponding European Patent Application No. 19787313.6.

(Continued)

*Primary Examiner* — Santiago Garcia
(74) *Attorney, Agent, or Firm* — Harness, Dickey & Pierce, P.L.C.

(57) ABSTRACT

An image analysis method for determining the biomedical state of a tissue sample. The method includes receiving a digital image of a tissue sample identifying the number and location of A-type cells and B-type cells, obtaining an observed relative distribution, obtaining a reference relative distribution of expected distances between reference A-type cells and reference B-type cells, computing a proximity score as a difference of the reference relative distribution and the observed relative distribution, computing a combined score comprising the proximity score and the density of the A-type cells and/or the density of the B-type cells, and using (Continued)

the combined score for determining the biomedical state of the tissue sample and/or outputting the combined score.

21 Claims, 14 Drawing Sheets

(56) References Cited

U.S. PATENT DOCUMENTS

| | | | |
|---|---|---|---|
| 2015/0309030 A1* | 10/2015 | Jirstrom | G01N 33/5091 600/1 |
| 2017/0270346 A1* | 9/2017 | Ascierto | G06T 7/0012 |
| 2018/0089495 A1 | 3/2018 | Black et al. | |
| 2018/0110423 A1* | 4/2018 | Presura | A61B 5/746 |
| 2018/0181835 A1 | 6/2018 | Fluxá Rodríguez et al. | |
| 2020/0050831 A1* | 2/2020 | Rogan | G06T 5/50 |
| 2020/0302603 A1* | 9/2020 | Barnes | G06T 7/162 |
| 2021/0201508 A1* | 7/2021 | Kotoku | G06N 3/08 |

OTHER PUBLICATIONS

Juliane M Kruger et al., "Combat or Surveillance? Evaluation of the heterogeneous Inflammatory Breast Cancer Microenvironment", The Journal of Pathology, vol. 229, No. 4, Feb. 15, 2013 (Feb. 15, 2013), pp. 569-578.

Yinyin Yuan, "Spatial Heterogeneity in the Tumor Microenvironment", Cold Spring Harbor Perspectives in Medecine, vol. 6, No. 8, Aug. 1, 2016 (Aug. 1, 2016).

A. Francesca Setiadi et al., "Quantitative, Architectural Analysis of Immune Cell Subsets in Tumor-Draining Lymph Nodes from Breast Cancer Patients and Healthy Lymph Nodes", PLOS One, vol. 5, No. 8, Aug. 25, 2010 (Aug. 25, 2010).

Andreas Heindl et al., "Mapping Spatial Heterogeneity in the Tumor Microenvironment: A New Era for Digital Pathology", Laboratory Investigation, vol. 95, No. 4, Jan. 19, 2015 (Jan. 19, 2015), pp. 377-384.

Office Action dated Apr. 28, 2022 issued in corresponding European patent application No. 19787313.6.

Philip M. Dixon, 'Ripley's K function,' *Encyclopedia of Environmetrics*, vol. 3, 2002, pp. 1796-1803.

Keith E. Steele, et al., 'Measuring multiple parameters of CD8+ tumor-inflating lymphocytes in human cancers by image analysis,' *Journal for ImmunoTherapy of Cancer*, vol. 6, No. 20, 2018, pp. 1-14.

International Preliminary Report on Patentability for PCT/EP2019/078819 dated May 6, 2021.

Chinese Office Action, dated Feb. 5, 2024, issued in Chinese Patent Application No. 2019800699604.

* cited by examiner

504 ○ MKI67+ (A- type cells/tumor cells)
506 ◇ CD8A+ (B- type cells/immune cells)

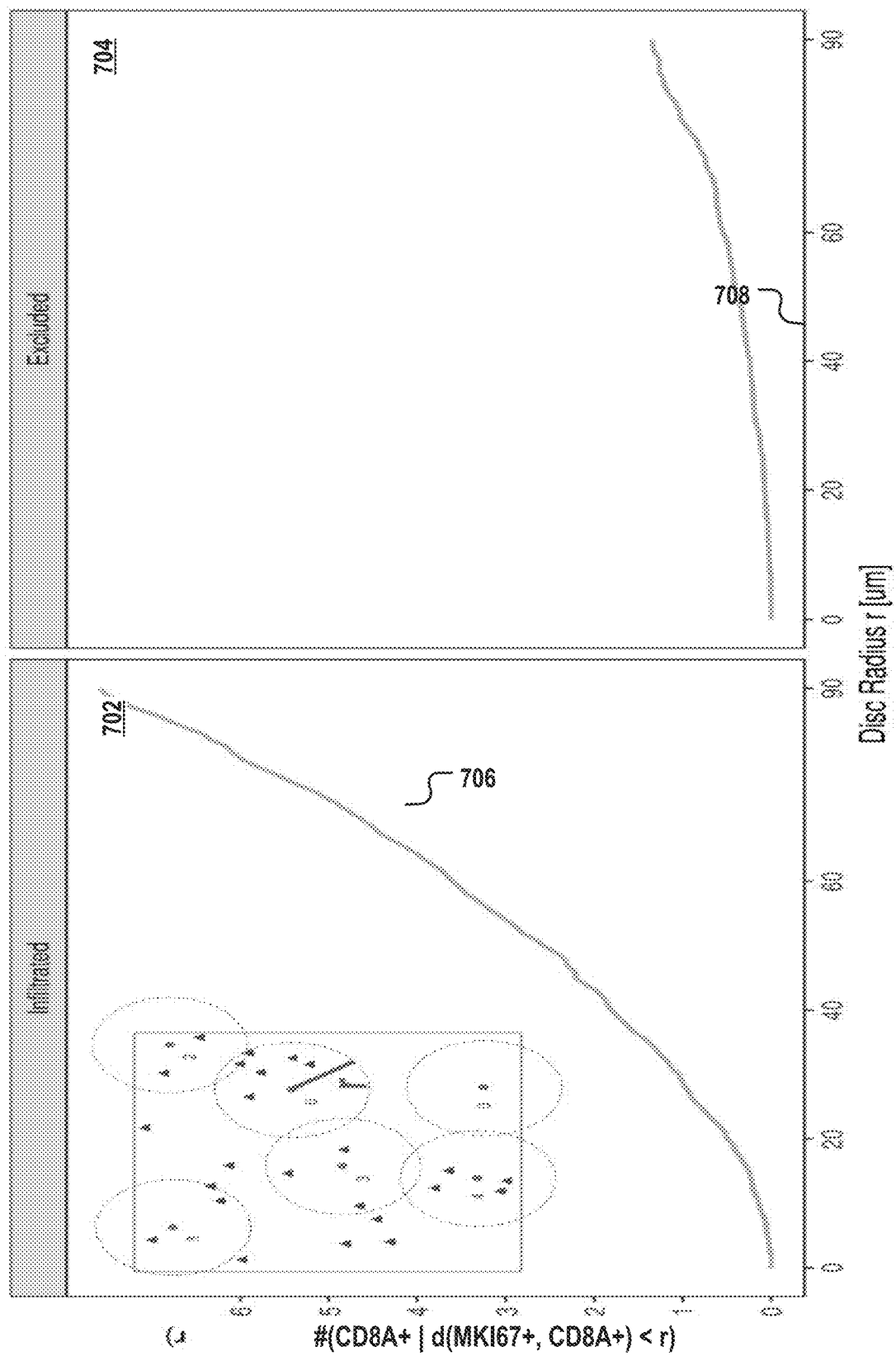

| Sample ID | 301310 | 301259 |
|---|---|---|
| Immuno-phenotype | Excluded | Infiltrated |
| Sample FOV<br>• 20x magnification<br>• Yellow: Tumor<br>• Blue: Stroma | ![804] | ![802] |
| CD8A+ Density | 315 cells / mm² | 318 cells / mm² |
| Proximity Score | -13.4 % | 31.8 % |

Fig. 9

DISTANCE-BASED TISSUE STATE DETERMINATION

FIELD OF THE INVENTION

The invention relates to the field of image analysis, and more particularly to the field of image-based classification of the biomedical state of a tissue sample.

BACKGROUND AND RELATED ART

Today, a plurality of different image analysis methods is used to automatically determine biomedical features of tissue samples. For example, image analysis is used for automatically identifying cells, for segmenting digital pathology images into background and tissue regions, and for automatically identifying and/or quantifying a biomedical condition, e.g. a particular disease.

An example is the detection of biomarkers, e.g. tumor markers, such as in the diagnosis of leukemia, breast cancer, colon cancer, and other types of cancer. It involves the labeling of cells with antibodies directed against protein which are specifically expressed or over-expressed in particular types of cells, e.g. tumor cells or other types of cells. By choosing appropriate antibodies, different types of cells can be accurately determined.

Immunophenotyping is a technique commonly used in basic science research and laboratory diagnostic purpose. It uses antibodies specifically directed against certain target molecules for identifying the "phenotype" of cells based on the expression level of one or more proteins. The cellular phenotype of one or more cells in a tissue may also be used for gaining insight on the biomedical condition of a tissue, e.g. whether the tissue is a healthy tissue, a primary tumor tissue or a metastatic tissue.

A common problem associated with many image analysis algorithms currently used for analyzing digital pathology images is that the expression level of certain proteins alone may allow the correct identification of cells of a particular cell type, but may not be sufficient for accurately, reproducibly and automatically determining the biomedical state of the tissue.

Steele K E et al. in "Measuring multiple parameters of CD8+ tumor-infiltrating lymphocytes in human cancers by image analysis" (J Immunother Cancer. 2018 Mar. 6; 6(1): 20. doi: 10.1186/s40425-018-0326-x) characterize the immune response to cancer based on the numbers and locations of CD8+ tumor-infiltrating lymphocytes (TILs). The immune response intensity is considered to be a parameter with high prognostic, pharmacodynamic, and predictive potential.

However, the ability of known approaches to provide accurate quantitative data in a way that also addresses the spatial aspects of cell distributions remains limited. In addition, the subjectivity and diversity of methods used for considering spatial relatedness conducted by multiple laboratories hinders the ability to compare histopathological results.

SUMMARY

It is an objective of the present invention to provide an improved method and image analysis system for the determination of the biomedical state of a tissue sample as specified in the independent claims. Embodiments of the invention are given in the dependent claims. Embodiments of the present invention can be freely combined with each other if they are not mutually exclusive.

In one aspect, the invention relates to an image analysis method for determining the biomedical state of a tissue sample. The method is implemented in an image analysis system. The method comprises:

receiving a digital image of a tissue sample;

analyzing the received image for identifying the number and location of A-type cells and B-type cells observed in an area of the received image, wherein the A-type and the B-type are different cell types;

analyzing the location of the A-type and B-type cells in the area for obtaining an observed relative distribution, the observed relative distribution being indicative of observed distances between the A-type cells and the B-type cells in the area;

obtaining a reference relative distribution, the reference relative distribution being indicative of expected distances between reference A-type cells and reference B-type cells;

computing a proximity score as a difference of the reference relative distribution and the observed relative distribution;

computing a combined score, the combined score comprising the proximity score and comprising the density of the A-type cells and/or the density of the B-type cells;

using the combined score for determining the biomedical state of the tissue sample and/or outputting the combined score to a user for enabling the user to determine the biomedical state of the tissue sample.

Said features may be advantageous, because contrary to state-of-the-art methods, the spatial distribution of different cell types is not determined subjectively by a pathologist. Rather, an observed relative distribution is compared with a reference relative distribution, i.e., with a distribution that represents expected distances between reference A-type cells and reference B-type cells in the area. The expected distances can be, for example, the distances that are expected assuming that the A-type cells and/or the B-type cells are distributed in accordance with a particular pre-defined mathematical distribution, e.g. a Poisson distribution. Alternatively, the expected distribution can be determined empirically based on an analysis of A-type and B-type cells in one or more other tissue samples having a known biomedical state. By defining a reference relative distribution and by computing a proximity score as a difference of the reference relative distribution and the observed relative distribution, a reproducible measure of the relative spatial location of the two different cell types in a tissue sample is provided. The proximity score may provide for a reproducible, quantitative measure of the deviation of the observed relative distributions/distances of A-type and B-type cells to the expected relative distributions/distances of A-type and B-type cells.

The proximity score may be considered as representing the "delta" between the observed relative distribution and the reference relative distribution. The proximity score integrates the spatial differences of the A-type-cell-B-type-cell distances represented in the observed and the reference relative distribution. Preferably, the proximity score is a single numerical data value that integrates the distance information obtained from a plurality of A-type and B-type cells. For example, the "delta" can be computed as a difference of radii as illustrated in FIG. 7 or a difference of areas as illustrated in FIG. 8.

In a further beneficial aspect, the proximity score may be a highly aggregated data value, because the proximity score value can be a single data value obtained by processing a plurality of observed and expected A-type-cell and B-type-cell distances. Hence, the information encoded in the spatial distribution of many hundreds and potentially many thousand cells can now be considered and can be used for reproducibly determining the biomedical state of a particular tissue. The information encoded in the spatial location of cells is complex, and so is their interpretation. By providing a single score value that is computed as a function of the observed and expected A-cell-B-cell distances, a parameter value is provided that encodes a lot of biomedical information and hence may have a high predictive relevance for various prediction tasks such as the determination of the biomedical state of a tissue or tissue region.

In a further beneficial aspect, the proximity score is combined with additional information, i.e., the density of the A-type and/or the B-type cells in the image area for providing a final, combined score. The combined score may be advantageous as it both "relative" information (i.e., the deviation of observed A-cell-B-cell distances from expected A-cell-B-cell distances) with "absolute" information, i.e., the density of the A-type or B-type cells in the examined image area. The combination of the absolute and relative information may be beneficial, because it may allow resolving also differences in the biomedical state of a tissue sample that could not be identified based on the proximity score alone or based on the density of one of the cell types alone. For example, there may be several different biomedical tissue states that have the same proximity score but can be distinguished based on differences in the absolute density of the B-type or A-type cells. In addition, or alternatively, there may be several different biomedical tissue states that have the same density of B-type cells (or A-type cells) but can be distinguished based on differences in the proximity score.

Embodiments of the invention may allow specifying a hypothesis that a particular biomedical state, e.g. a particular tumor type and stage, drives the observed distribution of cells away from an expected distribution (e.g. a random distribution such as the Poisson distribution) and allows easily testing this hypothesis by computing the proximity score. In case the proximity score is zero or close to zero, there is basically no difference of the observed relative distribution and the expected reference relative distribution and the hypothesis can be accepted. For example, the hypothesis could be that in case the tissue sample is a tumor tissue sample taken from a tumor of a particular type and stage, the tumor microenvironment drives the observed relative distribution of tumor cells (A-type cells) and immune cells (B-type cells) away from a random reference distribution.

Hence, the combined score may provide for a highly aggregated parameter that has a high predictive power and that may allow reproducibly characterizing spatial information related to the relative distribution of the A-type and B-type cells in a tissue. The proximity score and the combined score may have the further advantage that they can be used for characterizing the relative distribution of any two different cell types and hence can be used for automatically determining biomedical states related to many different biomedical questions. Hence, a highly reproducible, non-subjective but nevertheless versatile score value is provided that can be used for automatically, reproducibly and accurately determine the biomedical state of a tissue sample.

Embodiments of the invention may allow avoiding inconsistencies when the results of IHC biomarker analyses conducted by multiple laboratories are compared and allow for a better harmonization among laboratories.

Furthermore, the combined score has been observed to be able to capture more complex histopathological information than state of the art image-analysis based approaches for determining the biomedical tissue state.

According to embodiments, the cells of the one of the two cell types having the higher cell density in the image area are referred to as the A-type cells and the cells of the other cell type are referred to as the B-type cells.

According to preferred embodiments, the distances between the A-type cells and the B-type cells are measured starting from the A-type cells, and the density used for computing the combined score is the density of the B-type cells in the image area.

According to embodiments, the density of the reference A-type cells is identical or similar to the density of the observed A-type cells in the image area. For example, the reference A-type cells can be simulated in the same image area wherein the A-type cells were observed, whereby the number of simulated reference A-type cells is identical or similar (e.g. identical +/−10%) to the number of observed A-type cells in the image area. In addition, the density of the reference B-type cells is identical or similar to the density of the observed B-type cells in the image area. For example, the reference B-type cells can be simulated in the same image area wherein the B-type cells were observed, whereby the number of simulated reference B-type cells is identical or similar (e.g. identical +/−10%) to the number of observed B-type cells in the image area.

Alternatively, the reference A-type cells and reference B-type cells are cells having been observed in a reference tissue sample. The reference tissue sample is chosen such that it can be expected that the number and density of the A-type cells and B-type cells in the reference tissue sample is similar to the density of the A-type cells and B-type cells in the tissue sample depicted in the received image. This may ensure that differences in the observed and the reference relative distribution are caused by other factors than cell density.

According to embodiments, the obtaining of the observed relative distribution comprises, for each of the identified A-type cells (for example, tumor cells) observed in the image area:
  a) selecting said A-type cell as a center of a circle with radius 0;
  b) increasing the radius by one step for generating an increased cycle;
  c) determining the number of B-type cells contained in the cycle generated in step b);
  d) store the current radius of the circle in association with the number of B-type cells determined in step b) in a storage medium and repeat steps b), c) and d) until a termination criterion is reached; and
  e) select an unselected one of the A-type cells and continue with a) using said newly selected A-type cell until all A-type cells have been selected.

The associated radii and numbers of the observed B-type cells obtained for each of the identified A-type cells and radii are stored as the observed relative distribution.

For example, the termination criterion can be a maximum radius, a maximum number of steps, the reaching of a maximum execution time, or a maximum number of repeats. Said features may be advantageous as the step-wise increase of the radii may allow covering a large range of cell-cell distances with comparatively low computational effort. For example, the steps may be chosen such that the radius is increased in each step by a size of 1-100 μm, e.g. 10 μm. The radius may be increased e.g. until a predefined maximum radius is reached, e.g. about 500 μm, or about 200 μm. By selecting the size and hence the number of steps and cell counting operations, a discrete data set can be obtained that reflects the observed relative spatial distribution of A-type and B-type cells.

According to embodiments, the observed relative distribution is computed based on a bivariate Ripley's K(t) function of the A-type cells and B-type cells observed in the image area.

For example, Ripley's K function has been described by Philip M. Dixon, Volume 3, pp 1796-1803 in Encyclopedia of Environmetrics (ISBN 0471 899976) Edited by Abdel H. El-Shaarawi and Walter W. Piegorsch, John Wiley & Sons, Ltd, Chichester, 2002. A generalization of Ripley's K(t) function to more than one type of point (a multivariate spatial point process) is described in said document in formula (11) according to:

$$K_{i,j}(d) = \frac{1}{\lambda_i} E\left[\begin{array}{c}\text{number of type } j \text{ events within distance } d \text{ of}\\ \text{a randomly chosen type } i \text{ event}\end{array}\right]$$

This may be advantageous, because the Ripley's K(t) function allows recording and modeling relative spatial distributions of two or more point patterns in the two-dimensional space. It is comparatively fast and is an integral part of several computational tools, e.g. mathematical software like "R".

According to embodiments, the observed relative distribution is computed as according to:

$$K_{i,j}(r) = \frac{1}{\lambda_i} E[t(u, r, X^j) \mid u \in X^{(i)}]$$

where $K_{i,j}(r)$ is a bivariate Ripley's K(t) function,
wherein i is an occurrence of object type "observed A-type cell";
wherein j is an occurrence of object type "observed B-type cell";
where $\lambda_j$ is the density (number per image area) of observed B-type cells;
where $X^i$ is the totality of observed A-type cells identified within the image area;
where $X^j$ is the totality of observed B-type cells identified within the image area;
where $u \in X^{(i)}$ is a cell (also considered a "currently examined cell") being an observed A-type cell;
where r is a stepwise increased radius centered in an observed A-type cell;
wherein t is a function over u, r, and $X^j$ and counts the number of observed B-type cells within a circle of radius r around an observed A-type cell u in the image area;
where "$|u \in X^{(i)}$" means "over all u which are observed A-type cells";
where E is the expected value of t obtained over all u.

In general, the "expected value" E of t obtained over all u describes the expected value of a variable (t, in this case). For example, the expected value E can be computed as an average, e.g. a probability-weighted average of all possible values of t obtained over all u. Intuitively, E is something like the "average outcome". For example, E of t obtained over all u can be computed as the average t obtained over all u.

An "average" as used herein is a single number taken as representative of a list of numbers. The "average" can be, for example, the arithmetic mean, i.e., the sum of the numbers divided by how many numbers are being averaged. Alternatively, the average can be a median or mode. The average is a measure of central tendency of a set of numerical values.

According to embodiments, the observed relative distribution is computed based on a derivative of the bivariate Ripley's K(t) function of the A-type cells and B-type cells observed in the image area.

According to one example, the derivative bivariate Ripley's K(t) function is a linear or non-linear transformation of the bivariate Ripley's K(t) function. In particular, the derivative bivariate Ripley's K(t) function can be a linear transformation of the bivariate Ripley's K(t) function. The linear transformation can be, for example, the square root of $K_{i,j}$ over π according to:

$$L_{i,j}(r) = \sqrt{\frac{K_{i,j}(r)}{\pi}}.$$

$L_{i,j}(r)$ is also referred to as "L-function" or "Besag's L-function". The linear transformation approximately stabilizes the variance of the estimate value K when the process is Poisson, and also transforms the benchmark value $K_{i,j}(r) = \pi r^2$ to $L_{i,j}(r) = r$.

According to embodiments, the reference relative distribution is computed based on a bivariate Ripley's K(t) function of simulated A-type cells and simulated B-type cells in the image area.

According to embodiments, the obtaining of the reference relative distribution comprises:
computationally simulating a distribution of simulated reference A-type cells, the density of simulated reference A-type cells being identical to the density of A-type cells observed in the image area;
computationally simulating a distribution of simulated reference B-type cells in the area, the density of simulated reference B-type cells being identical to the density of B-type cells observed in the image area;
computing the reference relative distribution as a function of the computationally simulated distributions of the simulated reference A-type and simulated reference B-type cells, the reference relative distribution being indicative of distances between the simulated reference A-type cells and the simulated reference B-type cells in the area.

The computational generation of simulated reference A-type cells and simulated reference B-type cells in the image area (the "simulation" of A- and B-type cells and their distribution based on a predefined, expected distribution) may have the advantage that no additional (typically scarce) tissue is required as a reference, and that the distribution of the reference A-type and reference B-type cells is guaranteed to accurately represent the expected distribution provided the number of simulated reference A-type and reference B-type cells is high enough. Hence, the simulation of a "virtual" tissue image area comprising the expected (e.g. Poisson) distribution of simulated reference A-type and reference B-type cells is computationally cheap and does not require the acquisition and staining of one or more reference tissue samples for providing an empirical reference base and respective reference images. Furthermore, the simulation of reference A-type and B-type cell is highly flexible and allows to arbitrarily modify the simulated distribution. This may allow "fine-tuning" a biomedical hypothesis and may allow precisely defining complex bivariate co-distribution patterns that do not follow a Poisson distribution. For example, the complex co-distribution pattern could correspond to a high fraction of reference A-type cells having reference B-type neighbor cells in exactly two concentric "belts" around the reference A-type cells. Although such complex patterns may hardly be observed in nature, the simulation may allow generate "ideotypical", complex distributions that may hardly be observed in their "ideal" form in a real tissue sample, but which may nevertheless help formulating and checking a biological hypothesis related to the spatial distribution of cells in a tissue sample.

According to embodiments, the reference relative distribution is derived from the simulated distributions of the reference A-type and reference B-type cells, whereby the simulated reference A-type cell distribution and/or the simulated reference B-type cell distribution can be, for example, a Poisson distribution.

According to preferred embodiments, the distribution of simulated reference A-type cells is a Poisson distribution and the distribution of simulated reference B-type cells is a Poisson distribution.

The Poisson distribution is a discrete probability distribution that expresses the probability of a given number of events occurring in a fixed interval of time or space if these events occur with a known constant rate and independently of the time since the last event. The Poisson distribution can also be used for the number of events in other specified intervals such as distance, area or volume. If the occurrence of any particular type of event does not affect the occurrence probability of time of future events, i.e., if the observed events happen independently of one another, then a reasonable assumption is that the number of events occurring in a day obeys a Poisson distribution. Hence, by generating a Poisson-distributed set of simulated A-type cells in the image area and a Poisson-distributed set of simulated B-type cells in the image area and by determining the reference relative distribution of the simulated reference A-type and reference B-type cells, the hypothesis that the distribution of A-type cells is completely independent of the distribution of reference B-type cells and vice versa can be simulated and tested in respect to a currently examined tissue sample.

According to embodiments, the density of the simulated reference A-type cells in the area is identical or highly similar to the density of observed A-type cells in the area of the image. The term "highly similar" here means that the number of the simulated reference A-type cells in an image area is identical to the number of observed A-type cells in the area of the image +/−10%. The number of the simulated reference B-type cells in the area is identical or highly similar to the number of observed B-type cells in the area of the image.

This may be advantageous as it is ensured that the total number and the density of the simulated reference A-type and B-type cells in the image area is identical to or highly similar to the respective number and density of observed cells. Hence, any deviation of the observed relative distribution from the reference relative distribution is not caused by any deviation in the number or density of the simulated cells, but is rather solely caused by differences in the relative spatial distribution of the cells of the two cell types. Hence, although the reference relative distribution may be based on simulated reference A-type and B-type cells, this simulation is strictly bound to the density of A-type and B-type cells observed in the tissue sample depicted in the image area. This may allow for performing a tissue-sample specific simulation that allows accurately determining any deviation in the relative spatial distribution of the cells of the two cell types in the tissue sample compared to the expected, simulated distribution. The differences in the spatial distribution from a simulation-based reference distribution are not affected by any other disturbing factors that may be of relevance when using a reference tissue sample for empirically creating a reference relative distribution.

According to embodiments, the computing of the reference relative distribution as a function of the computationally simulated distributions of the reference A-type and reference B-type cells comprises:

For each of the randomly distributed simulated reference A-type cells (e.g. tumor cells), the following steps are performed:
  a) selecting said simulated reference A-type cell as a center of a circle with radius 0;
  b) increasing the radius by one step for generating an increased cycle;
  c) determining the number of simulated reference B-type cells (e.g. immune cells) contained in the cycle generated in step b);
  d) store the current radius of the circle in association with the number of simulated reference B-type cells determined in step b) in a storage medium and repeat steps b), c) and d) until a termination criterion is reached; and
  e) select an unselected one of the simulated reference A-type cells and continue with a) using said newly selected simulated reference A-type cell until all simulated reference A-type cells have been selected;

The method further comprises providing the associated radii and numbers of simulated reference B-type cells as the reference relative distribution.

The advantages of this step-wise computation of reference B-type cell counts within step-wise increasing circles around each reference A-type cell may have the advantages described already for the analogous determination of radii and numbers of B-type cells stored during the computation of the observed relative distribution.

According to embodiments, the reference relative distribution is computed as according to:

$$K_{i,j}(r) = \frac{1}{\lambda_i} E[t(u, r, X^j) \mid u \in X^{(i)}]$$

where $K_{i,j}(r)$ is a bivariate Ripley's K(t) function,
wherein i is an occurrence of object type "simulated reference A-type cell";
wherein j is an occurrence of object type "simulated reference B-type cell";
where $\lambda_j$ is the density (number per image area) of simulated reference B-type cells;
where $X^i$ is the totality of simulated reference A-type cells within the image area;
where $X^j$ is the totality of simulated reference B-type cells within the image area within the image area;
where $u \in X^{(i)}$ is a cell being a simulated reference A-type cell;
where r is a stepwise increased radius centered in a simulated reference A-type cell;

wherein t is a function over u, r, and $X^j$ and counts the number of simulated reference B-type cells within a circle of radius r around a simulated reference A-type cell u in the image area;

where "$|u \in X^{(i)}$" means "over all u which are simulated reference A-type cells";

where E is the value of t expected over all u.

As defined above, the "expected value" E of t obtained over all u describes the expected value of a variable (t, in this case). For example, the expected value E can be computed as an average, e.g. a probability-weighted average of all possible values of t obtained over all u. For example, E of t obtained over all u can be computed as the average t obtained over all u.

According to embodiments, the reference relative distribution is computed based on a derivative of the bivariate Ripley's K(t) function of the simulated A-type cells and the simulated B-type cells. According to one example, the derivative bivariate Ripley's K(t) function is a linear or non-linear transformation of the bivariate Ripley's K(t) function. In particular, the derivative bivariate Ripley's K(t) function can be a linear transformation of the bivariate Ripley's K(t) function. The linear transformation can be, for example, the "L-function" or "Besag's L-function computed as the square root of $K_{i,j}$ over $\pi$ according to:

$$L_{i,j}(r) = \sqrt{\frac{K_{i,j}(r)}{\pi}}.$$

According to embodiments, the reference relative distribution and/or the observed relative distribution are computed as a version of Ripley's K(t) function as described in formula (12) in Philip M. Dixon's above mentioned publication according to:

$$\hat{K}\_(i,j)(d) = (\hat{\lambda}_i \hat{\lambda}_j A)^{-1} \Sigma_k w(i_k, j_l) Iw(d_{i_k, j_l} < t)$$

where $w(i_k, j_l)$ is the fraction of the circumference of a circle centered at the kth location of process l with radius $d_{ik,jl}$ that lies inside the study area.

According to embodiments, the obtaining of the reference relative distribution comprises computing a plurality of initial reference relative distributions in accordance with any one of the embodiments and examples of the invention described herein. Then, the method comprises computing an average reference relative distribution from the plurality of initial reference relative distributions and using the average reference relative distribution as the reference relative distribution.

Preferably, the proximity score is computed as a difference (the "delta") between the average reference relative distribution and the observed relative distribution. This includes a difference between parameter values associated with the average reference relative distribution and the observed relative distribution. For example, the difference could be a difference of radii respectively associated with the two distributions as illustrated in FIG. 7 or a difference of areas as illustrated in FIG. 8.

For example, a number n initial reference relative distributions can be computed, wherein n is a number that is preferably larger than 10, more preferably larger than 30, e.g. 39. Then, an "average relative distribution" is computed by computing, for each of a plurality of radii used for counting B-type cells in the spatial neighborhood of A-type cells (or vice versa) defined by circles having the respective radii, the average number of B-type cells observed in a circle of a respective radius. For example, in case n=5 and the four examined radii would be 10 μm, 30 μm, 60 μm and 100 μm, then a first average B-cell number would be computed for radius 10 μm from 5 values obtained from the respective n initial relative distributions, a second average B-cell number would be computed for radius 30 μm from 5 values obtained from the respective n initial relative distributions and so on until an average B-type cell count is computed for each examined radius.

According to some embodiments, for each of the radii (or each of a plurality of other predefined distances defining the spatial neighborhood of an A-type-cell that is used for computing a relative distribution), not only the average reference B-type cell count (or reference A-type cell count if the number of A-type cells in the spatial neighborhood of reference B-type-cells is examined) is computed, but also the minimum and maximum reference B-type cell count in any one of the initial reference relative distributions and for any one of a plurality of radii/distances examined. The average reference relative distribution is used for computing the proximity score and the min/max cell count is used for computing a confidence band wherein the min/max values represent the borders of the confidence band and wherein the width of the band illustrates a "region of significance" in a plot. If the observed relative distribution lies within the confidence belt, the observed relative distribution is considered as being identical or at least not significantly different from the reference relative distribution.

For example, n=39 initial reference relative distributions can be computed based on simulations of Poisson distributed reference cells of type A and type B, respectively, whereby the density of the simulated reference A-type cells is identical to the density of the "real" A-type cells observed in the image area of the tissue sample and wherein the cell density of the simulated reference B-type cells is identical to the density of the "real" B-type cells observed in the image area. The simulation is performed for a given density of A-type and B-type cells 39 times to obtain "p-values" in combination with the observed relative distribution 1/(39+1) =0.025=alpha/2, wherein alpha is a predefined significance level. Then, a 2D plot is created wherein one dimension represents the cell distance and one dimension represents the cell count. Then, the average reference relative distribution that is obtained by averaging the 39 initial reference distributions is drawn in the 2D plot. In addition, a "confidence band" is plotted, wherein the lower border of the band is computed as the minimum cell count observed for a particular distance (e.g. a radius) in all the 39 initial reference relative distributions and wherein the upper border of the band is computed as the maximum cell count observed for a particular distance (e.g. a radius) in all the 39 initial reference relative distributions. Hence, for each distance/ radius r around the cells of a particular cell type (e.g. the A-type cells), the minimum, maximum and average observed cell count of the respectively other cell type (e.g. B-type cells) derived from all 39 simulations is plotted. In addition, the observed relative distribution is plotted in the 2D plot. This may be beneficial is it allows a human user to intuitively assess whether the observed relative distribution is inside or outside of the confidence band that surrounds the average reference relative distribution. If the observed reference relative distribution is outside of the confidence band, the observed reference relative distribution is different from the average reference relative distribution at a predefined significance level of alpha, whereby alpha can be, for example, 0.05 (0.025 two-sided).

The above mentioned 2D plot may also be referred to as "significance plot". Examples of a significance plot are provided in FIG. 7. The significance plot can comprise a first dimension representing a radius of a circle drawn around each tumor cell within the image area and its nearest immune cell and a second dimension representing the number of immune cells located within said circle, the number being normalized by the densities of the immune cells and tumor cells. The plot may comprise a confidence belt surrounding the reference relative distribution, the confidence belt being indicative of a confidence interval for the numbers of immune cells observed for each radius value according to the plotted reference relative distribution. According to preferred embodiments, the confidence belt represents the 95% confidence band coming from the 39 simulations (it is possible to show that these 39 simulations for a particular type of biomedical state determination task correspond to 95% confidence). The observed relative distribution is also plotted in the significance plot. The observed relative distribution can be graphically represented a curve visually indicating the number of identified immune cells having been observed to occur in a respective circle around the observed tumor cells, said number being normalized by the densities of the immune cells and tumor cells.

According to other embodiments, the reference relative distribution is not obtained by simulating a particular cell distribution, but rather is obtained empirically from one or more other tissue samples of known biomedical state and respective digital pathology images of said samples.

According to other embodiments, the obtaining of the reference relative distribution comprises:
  receiving a further digital image for each of one or more further tissue samples, each further tissue sample being derived from a tissue of known biomedical state; The further digital image can also be referred to as "reference image" and the further tissue sample can be referred to as "reference sample";
  analyzing each received further image for identifying the number and location of observed reference A-type cells and observed reference B-type cells in an area of the received further image;
  analyzing the location of the observed reference A-type and the observed reference B-type cells in the area of each further image for obtaining a an observed reference relative distribution, the observed reference relative distribution being indicative of observed distances between the reference A-type cells and the reference B-type cells observed in the area of the further received image; and
  using the observed reference relative distribution as the reference relative distribution.

Hence, the generation of the reference relative distribution as described in the above embodiment is not based on a computational simulation, but rather on the evaluation of the relative spatial distribution of reference A-type and reference B-type cells in one or more other tissue samples having a known biomedical state.

This may be advantageous in case no suitable simulation software is available or in case a mathematical function for generating a particular relative distribution that represents a known biomedical state is not yet been defined and implemented in software. For example, if the biomedical state, e.g. a cancer type and stage or an immune-cell-infiltration level of a particular tumor tissue, has been clearly identified by one or more human pathologists, it may be more convenient to use the empirical information implicitly contained in such further tissue samples for providing a reference relative distribution than performing a computational simulation. For example, in case the relative spatial distribution of the two different cell types in the tissue samples with the known biomedical state does not follow a Poisson distribution, it may be easier to simply determine the relative distribution of the cells of the two cell types empirically in order to obtain a reference relative distribution that represents a "hypothesis" that a tissue sample having a similar relative distribution also has the biomedical state of the one or more other tissue samples from which the empirically determined reference relative distribution is derived.

The empirically determined reference relative distribution can be obtained, for example, from the tissue sample of the same "currently examined" organism as the tissue sample from which the observed relative distribution is obtained using image analysis methods. For example, the "other tissue sample" can be a tissue sample adjacent to the tissue sample depicted in the digital image from which the observed relative distribution is obtained. Alternatively, the other tissue sample can be derived from another organism than the "currently examined" organism, whereby the other organism is preferably from the same species or a closely related species than the "currently examined" organism. It is merely required that the biomedical state of the other organism is known as this ensures that the reference relative distribution obtained from said other organism represents a particular, known biomedical state.

It is also possible that an initial reference relative distribution is empirically determined from each of a plurality of other tissue samples having the same known biomedical state. Then, an average reference relative distribution is obtained by computing the average of each of the empirically determined initial reference relative distributions. According to some embodiments, the obtaining of the average reference relative distribution comprises performing a curve fitting.

The reference relative distribution or the initial reference relative distributions can be obtained from the one or more other tissue samples via image analysis in the same way as the observed relative distribution is obtained.

According to one embodiment, a pathologist may manually annotate the biomedical state of a reference tissue sample to an image of said reference tissue sample of a patient. A reference relative distribution is obtained based on an image analysis of the image of the reference tissue sample. A plurality of tissue samples adjacent to the reference tissue sample is obtained from the patient. From each of a plurality of adjacent other tissue samples, a respective digital image may be acquired that is automatically analyzed for computing an observed relative distribution. By comparing the observed relative distribution of each of the adjacent tissue samples with the reference relative distribution of the reference tissue sample, it can be determined whether the tissue of the patient from which the multiple tissue samples including the reference sample was derived shows a homogeneous or heterogeneous spatial relationship and distribution of the A-type and B-type cells.

According to embodiments, the computing of the proximity score as a difference of the reference relative distribution and the observed relative distribution comprises:
  providing a predefined number representing a predefined minimum number of B-type cells (e.g. "1");
  identifying within the observed relative distribution an observed radius $r_{o\text{-}min}$, wherein the observed radius $r_{o\text{-}min}$ is a radius that—if drawn around each one of the observed A-type cells, would define a circle that comprises on average the predefined number of the observed B-type cells;

identifying within the reference relative distribution a reference radius $r_{r-min}$, wherein the reference radius $r_{r-min}$ is a radius that—if drawn around each one of A-type cells that were simulated or that were observed in further digital images of a further tissue sample for providing the reference relative distribution, would define a circle that comprises on average the predefined number of B-type cells that were simulated or that were observed in further digital images of a further tissue sample for providing the reference relative distribution;

computing the proximity score as a function of the observed radius $r_{o-min}$ and the reference radius $r_{r-min}$. Preferably, the function is the difference between the observed radius and the reference radius.

For example, the predefined number representing a predefined minimum number of B-type cells can be any number larger than 0. Preferably, the predefined minimum number is 1.

Said features may be advantageous as the complexity of the information contained in the observed and in the reference relative distribution is reduced in some first step to two particular distance measures, i.e., two particular radii, and is then reduced in a further step to a proximity score value. In the simplest case, the proximity score is computed as the difference of the two radii. However, the computation of the proximity score may also be more complex and comprise, for example, additional normalization steps, steps for performing error corrections, steps for multiplying the difference of the two radii with an error correction factor or the like. The proximity score may be a numerical value.

According to alternative embodiments, the computing of the proximity score as a difference of the reference relative distribution and the observed relative distribution comprises:

defining a first distance threshold (t1); for example, the first difference threshold can have a value between 10 and 20 µm, e.g. 15 µm;

defining a second distance threshold (t2); for example, the second difference threshold can have a value between 30 and 40 µm, e.g. 35 µm;

plotting the reference relative distribution and the observed relative distribution respectively in the form of a curve in a plot, wherein a first dimension of the plot represents a radius r used for determining the observed and reference relative distributions, wherein a second dimension of the plot represents the number of B-type cells closer than r to an A-type cell (or vice versa);

identifying a first area in the plot, the first area being defined by the first and second thresholds, a base line corresponding to a second dimension value of zero, and an observed relative distribution curve segment between the first and second thresholds;

identifying a second area in the plot, the second area being defined by the first and second thresholds, the base line corresponding to a second dimension value of zero, and a reference relative distribution curve segment between the first and second thresholds;

computing the proximity score as a function of the first area and the second area, the function being in particular the difference between the first and the second area.

In some embodiments, the proximity score is normalized within a predefined scale range. This may allow mapping the proximity score obtained for the currently examined tissue sample on a predefined proximity score scale. The scale with the score value can be displayed to a user, e.g. via a display of the image analysis system and may allow the user to quickly and intuitively asses how much the relative distribution of A-type and B-type cells in the currently examined tissue sample deviates from a reference relative distribution of A-type and B-type cells, whereby the reference relative distribution represents a random distribution or any other type of expected relative distribution.

The difference of the radii where a predefined minimum B-type cell count is respectively observed is indicative of the deviation of the observed distribution from an expected, e.g. random, relative distribution of A-type and B-type cells.

According to some embodiments, the Ripley's K of the observed relative distribution is multiplied by the cell density of B-type cells observed in the image area. In addition, the Ripley's K of the reference relative distribution is multiplied by the cell density of B-type cells that were simulated or that were observed an image area of the same size in an image of a reference tissue sample to obtain reference cell counts of B-type cells in the neighborhood of A-type cells. Then, the difference of the observed and the reference B-type cell count is computed.

According to some embodiments, the method comprises graphically representing the observed relative distribution as an observed-distribution curve in a 2D plot whose first dimension represents the radius r (Ro) and whose second dimension represents the number of observed B-type cells associated with said radius. The 2D plot is displayed on a display device of the image analysis system.

In addition, or alternatively, the method comprises graphically representing the reference relative distribution as a reference-distribution curve in a 2D plot whose first dimension represents the radius r (Rs) and whose second dimension represents the number of simulated B-type cells associated with said radius.

Preferably, the observed-distribution curve and the reference-distribution curve are plotted into the same 2D plot as this eases the comparison of the two cures by a user.

Then, the 2D plot comprising the observed-distribution curve and/or the reference-distribution curve is then displayed on a display device of the image analysis system. Preferably, also a confidence belt is computed from minimum and maximum values of a plurality of simulated or empirically obtained initial reference relative distributions and the confidence belt is also plotted into the 2D plot such that the confidence belt surrounds the reference-distribution curve.

This may be advantageous as the 2D plot allows even users with limited statistical knowledge to intuitively and quickly assess whether or not an observed relative distribution is significantly different from a given reference relative distribution.

According to embodiments, the A-type cells are tumor cells and/or the B-type cells are immune cells. Preferably, the relative distribution is obtained by counting, in the spatial neighborhood of each of the tumor cells, the number of immune cells observed or simulated in said spatial neighborhood. This approach may be preferable for most of the tumor types where the tumor cells have a larger density than the immune cells as this approach may ensure that a sufficient number of "count results" is obtained. The number of "count results corresponds to the number of tumor cells and may often be "zero" in case the immune cells are very rare in the tissue.

According to other embodiments, the B-type cells are tumor cells and/or the A-type cells are immune cells. Preferably, the relative distribution is obtained by counting, in the spatial neighborhood of each of the immune cells, the number of tumor cells observed or simulated in said spatial neighborhood. This approach may be preferable for some tumor types where the immune cells have a larger density than the tumor cells or are for other reasons better starting points for determining the number of cells of the other cell type in their respective neighborhood.

According to embodiments, the tissue sample is a tumor tissue sample and the determination of the biomedical state of the tissue sample comprises determining the infiltration state of the tumor tissue depicted in the area of the received digital image with immune cells.

This may be advantageous because the determination of the infiltration state is an important prognostic parameter for characterizing a tumor and for selecting appropriate treatment options. The density of immune cells and tumor cells alone is not sufficient for distinguishing e.g. tumor tissue showing an "excluded" infiltration pattern and tumor tissue showing an "infiltrated" infiltration pattern. Likewise, the spatial proximity of tumor and immune cells alone may not be sufficient for distinguishing e.g. tumor tissue showing an "excluded" infiltration pattern and tumor tissue showing an "deserted" infiltration pattern. However, a combined score comprising density as well as spatial proximity information allows distinguishing many different infiltration states like "infiltrated", "excluded" and "deserted". Hence, the computation of a combined score as described herein is particularly useful in the context of determining the immune-cell-infiltration state of tumor tissue. Immune set point prior to immunotherapy may be highly helpful for achieving a truly personalized treatment. The combined score may allow for a better characterization of oncology patients in order to predict the susceptibility to drugs of different mode of actions and to evaluate response to a given immunotherapy and provide decision support for continuation of treatment, need of additional drugs per shift to another drug with another mode of action.

The proximity value can be a numerical value that can be represented by a particular point on a continuous scale, thereby providing more granularity and sensitivity than manually defined classifications currently in use. This may be highly beneficial, since the majority of cases cannot be clearly assigned to a particular, extreme state like "infiltrated", "deserted" or "excluded", but rather belong to a moderately inflamed state and the difference between a slightly inflamed and the slightly excluded tumor may be very hard to identify and to characterize in a clear, reproducible and non-subjective manner.

For example, the tumor cells can be identified in a digital image of a tissue sample by staining the tissue sample with one or more tumor marker specific stains (e.g. stains selectively staining cytokeratins, BRAC1, etc.) and applying image analysis methods for identifying cells expressing said biomarkers as the tumor cells.

Optionally, the tissue can be stained with immune-cell specific stains and the image analysis method is performed such that selectively non-immune cells expressing a tumor marker or a proliferation marker are identified as the tumor cells. For example, cells expressing the biomarker Ki67 and which do not express the lymphohoid biomarkers CD8 (or CD3) are identified as tumor cells.

In some cases, it has been observed that not all tumor cells are expressing Ki67. Nevertheless, it has been observed that Ki67+ cells provide representative samples of tumor cells and provide accurate results.

According to embodiments, the immune cells are identified as cells expressing a biomarker that is selectively expressed in an immune cell. For example, cytotoxic T cells, can be identified as CD8A+ cells.

According to some embodiments, the area in the received digital image wherein the cells are identified comprises a sub-area that is manually or automatically annotated as a "tumor region". In this case, preferably only cells expressing a proliferation biomarker like Ki67 and/or a tumor marker which in addition lie within this "tumor region" are identified as "tumor cells". And only cells expressing an immune cell specific biomarker which in addition lie within this "tumor region" are identified as "tumor cells". This may ensure that biomedical particularities of the tissue outside of the tumor region does not have an impact on the analysis result whether or not the spatial relative distribution of tumor cells and immune cells is identical to an expected relative distribution or not.

According to some embodiments, the method further comprises graphically representing the combined score as symbol within a 2D score plot. A first dimension of the 2D score plot represents the proximity score and wherein a second dimension of the 2D score plot represents the density of the B-type cells or the density of the A-type cells. Preferably, the density of the B-type cells is plotted, whereby the B-type cells are immune cells and the A-type cells are tumor cells. The 2D score plot is output on a display of the image analysis system for enabling a human to determine the biomedical state of the tissue sample. In addition, or alternatively, the determination of the biomedical state of the tissue sample is performed by the image analysis system by automatically identifying the biomedical state of the tissue sample within a limited set of predefined biomedical states or within a predefined, continuous spectrum of biomedical states. The identified biomedical state is then output, e.g. displayed, as the determined biomedical state.

Preferably, the density represented by one dimension of the 2D score plot is the observed density of the one of the two types of cells having the lower density, e.g. the B-type cells. Preferably, the B-type cells are the one of the two cell types whose number is counted in the neighborhood of each A-type cell.

The determined biomedical state of the tissue can be identified in or mapped to a continuous spectrum of biomedical states. In addition, or alternatively, the biomedical state may be one out of a limited set of predefined, discrete biomedical tissue states.

According to some embodiments, the determination of the immune-cell-infiltration-state of a tumor sample comprises separating tumors into different, predefined infiltration states, e.g. "deserted", "excluded" or "inflamed". For example, thresholds for the combined score value can be obtained from empirical data of a plurality of tissue samples and the obtained thresholds of the combined score can be used for classifying the tissue sample depicted in the image area into one of the predefined infiltration states.

According to other embodiments, the determination of the infiltration state comprises identifying the infiltration state of the tissue sample on a predefined continuous spectrum representing the grade of inflammation in the tumor. The extremes of the spectrum represent tumors highly inflamed versus completely devoid of immune cells. In this case, not one out of a predefined, limited set of infiltration states is identified, but rather a continuous score is provided that allows to map the tumor in the depicted image area on the spectrum between the most extreme infiltration states.

Infiltration of tumors by immune cells is triggered by the presentation of mutated tumor antigens presented in the context of MHC on tumor cell surface. The tumor antigen is recognized as non-self and eliminated by mainly natural killer cells and cytotoxic T-cells. The elimination is dependent on intricate signaling pathways that can be modified or hampered by the tumor. This balance between tumor progression and the immune system's attempt to kill the tumor cells has been described as the elimination-equilibrium-escape mechanism. The current development in immunotherapy has a huge potential to change the dismal prognosis for many cancer patients by changing the tumor-immune microenvironment in favor of the tumor cell elimination side of the balance.

The field has witnessed many proposals for the immunophenotyping of tumors to measure and describe the status of the elimination-equilibrium-escape balance, but no consensus has been reached. The main hurdle to overcome is characterized by the lack of a deeper understanding of how the theory of a continuum between elimination and escape can be translated into biologically meaningful information presented in histological tumor samples. Manual scoring systems propose different numbers of classes the spectrum should be divided into and in general there is no agreement on how to find thresholds or objective definitions for these categories. Embodiments of the invention allow overcoming these obstacles and allow providing an automated, calibrated and discrete measure of the infiltration state of a tumor based on both presence and distribution of tumor-infiltrating immune cells. Hence, embodiments of the invention allow capturing information on biological tendencies such as if the immune system's balance is weighted towards elimination of a tumor escape as well as if the immune system is overall activated or silenced.

According to embodiments, the image analysis method further comprises receiving a digital image of a tissue sample from each of a plurality of different patients; computing a combined score for each of the patients using the respectively received image in accordance with any one of the previous claims; and graphically representing the biomedical state of each patient by a respective, biomedical-state-specific symbol, on a 2D score plot, the position of the symbol of each patient in the plot depending on the B-type cell density and the proximity score computed for the patient.

This may be advantageous, as a user is provided with a plot that allows to quickly and intuitively determine the biomedical state of a tissue sample, e.g. the immune cell infiltration state, based on the x and y coordinates of a point in the plot, whereby the point represents the tissue sample and the x and y coordinates of the plot represent the proximity score and the immune observed B-type cell density in the tissue sample.

The immune infiltrate in tumors is the host's response to something foreign in the body. It is triggered by the presence of tumor antigens (mutated proteins) presented on tumor cells. Tumors can be devoid of immune cells if the immune system is suppressed or if the tumor downregulation the expression of tumor antigens. In reality the amount of immune infiltrate is seen as a spectrum from none to heavily infiltrated.

According to embodiments, the identified biomedical state is selected from a group comprising:

"inflamed", wherein "inflamed" is indicative of an immunological tissue state in which immune cells have a significantly increased cell density being indicative of a heavy infiltration of the tumor tissue with immune cells in all compartments of the tumor, wherein the higher the observed immune cell density in the image area and the higher the proximity score, the higher the likelihood of a tissue sample of being classified as "inflamed";

"excluded", wherein "excluded" is indicative of an immunological tissue state in which immune cells are present in the tissue sample but are hindered to come into close contact to the tumor cells, whereby the immune cells are concentrated at the invasive margin and/or in the intratumoral stroma but separated from the tumor cells, wherein the higher the observed immune cell density in the image area and the lower the proximity score, the higher the likelihood of a tissue sample of being classified as "excluded";

"desert", wherein "desert" is indicative of an immunological tissue state in which immune cells in a tumorous tissue region have a cell density that is zero or close to zero, wherein the lower the observed immune cell density in the image area, the higher the likelihood of a tissue sample of being classified as "desert" irrespective of the height of the proximity score.

Applicant has observed that many tumors display a picture that doesn't fit completely into any of the above mentioned extreme categories. Hence, the computation of a combined score value is advantageous as it is a combination of two continuous numerical score value (proximity score, cell density) and hence allows to provide an accurate prediction/determination of a biomedical state of a tissue based on two important features: the density indicates if an organism is able to elicit an immune response. The proximity score indicates if the tumor is immunogenic and adapted to attract immune cells. If not, the tumor may have developed means to avoid immune cells (e.g. HLA-G up-regulation or cytokine production that would make immune cells dormant or stimulation of regulatory immune subsets).

According to embodiments, in case the biomedical state of the tissue sample is determined to be the infiltration state "inflamed", the image analysis method comprises outputting, via a user interface, a treatment recommendation to prescribe a drug acting as checkpoint inhibitor, e.g. anti-PD-L1/PD-1, CTL4.

In addition, or alternatively, in case the biomedical state of the tissue sample is determined to be the infiltration state "excluded", the image analysis method comprises outputting, via a user interface, a treatment recommendation to prescribe a drug adapted to attract immune cells closer to tumor cells. For example, this drug could be a bispecific antibody directed against the tumor cells. An example of this bispecific antibody is CEA-TCB that binds simultaneously with one arm to CD3 on T-cells and with two arms to CEA on tumor cells, thereby bringing T-cells into close proximity to the cancer cells. This leads to T-cell activation and subsequent tumor cell killing. Another example for suitable drugs to be recommended in case of an "excluded" infiltration state would be a drug that breaks tumor escape mechanisms, like a drug that blocks HLA-G or up-regulates MHC I.

In addition, or alternatively, in case the biomedical state of the tissue sample is determined to be the infiltration state "deserted", the image analysis method comprises outputting, via a user interface, a treatment recommendation to prescribe a drug adapted to generically boost the immune system, e.g. IL-2.

According to embodiments, the shapes of the tumor cells and immune cells within the image area are stored in form of points in a spatial database. The simulated and measured distances are identified using spatial database operations provided by the spatial DBMS, in particular WITHIN_DIS- TANCE( ) and DISTANCE( ) operations. This may be advantageous as the computation of the relative distributions can greatly be accelerated. This may in particular be of reference if a large number of initial reference relative distributions have to be simulated in order to provide a confidence belt of a desired width. For example, the SDO_GEOM functionality of the Oracle Spatial DBMS can be used.

According to other embodiments, the scores are computed outside of the DB using R.

According to embodiments, the expected distribution is indicative of distances between reference A-type cells and reference B-type cells that are expected under the assumption of a Poisson distribution of the A-type cells and the B-type cells in the area. Preferably, the assumption further is based on identical densities of observed A-type cells and reference A-type cells and of identical densities of observed B-type cells and reference B-type cells.

In a further aspect, the invention relates to a method of determining the efficacy of a drug for treating a particular type of cancer. The method comprises:
  receiving a plurality of first digital images, each first image depicting a tissue sample of a respective organism having the particular type of cancer before said organism was treated with the drug;
  computing, from an image area of each of the first digital images, a first combined score in accordance with any one of the previous claims, wherein the biomedical state is an immune-cell-infiltration state of a tumor, the A-type cells are tumor cells and the B-type cells are cancer cells;
  receiving a plurality of second digital images, each second image depicting a tissue sample of a respective organism having the particular type of cancer after said organism was treated with the drug;
  computing, from an image area of each of the second digital images, a second combined score according to any one of the previous claims, wherein the biomedical state is an infiltration state, the A-type cells are tumor cells and the B-type cells are cancer cells;
  displaying a 2D score plot on a display device, wherein each first combined score is represented by a first symbol in the 2D score plot, wherein each second combined score is represented by a second symbol in the 2D score plot, wherein the position of the first and second symbols in the plot depend on the immune cell density observed in the image area of the respective images and on the proximity score computed for the image area of the respective images, wherein first and second symbols representing the same organism are visually linked in the 2D plot score for visualizing any shift in the x and/or y coordinates from any one of the first symbols to its respectively linked second symbol.

This may be advantageous as the above described approach allows visually representing the efficacy of a particular drug tested on a plurality of different patients, whereby the effect of the drug on the spatial distribution of immune cells and tumor cells are visualized. Already the visual representation of a modification of the relative spatial distribution of cells in a single patient is a challenge. Here, the response of a plurality of patients to a particular drug in respect to the modification of the relative spatial distribution of tumor and immune cells is visualized, thereby allowing medical professionals to easily assess whether or not a drug had an effect and to assess which type of biomedical state (e.g. tumor infiltration state) was promoted or suppressed by the drug. The visually linking may be performed, for example, by connecting symbols (e.g. circles, triangles, etc.) derived from the same patient with a line.

In a further aspect, the invention relates to a storage medium comprising computer-interpretable instructions which, when executed by a processor, cause the processor to perform an image analysis method according to any one of the embodiments and examples described herein.

In a further aspect, the invention relates to an image analysis system for determining the biomedical state of a tissue sample. The system comprises a processor and computer-interpretable instructions configured to cause the processor executing the instructions to perform a method comprising:
  receiving a digital image of the tissue sample;
  analyzing the received image for identifying the number and location of A-type cells and B-type cells observed in an area of the received image, wherein the A-type and the B-type are different cell types;
  analyzing the location of the A-type and B-type cells in the area for obtaining an observed relative distribution, the observed relative distribution being indicative of observed distances between the A-type cells and the B-type cells in the area;
  obtaining a reference relative distribution, the reference relative distribution being indicative of expected distances between reference A-type cells and reference B-type cells;
  computing a proximity score as a difference of the reference relative distribution and the observed relative distribution;
  computing a combined score, the combined score comprising the proximity score and comprising the density of the A-type cells and/or the density of the B-type cells;
  using the combined score for determining the biomedical state of the tissue sample and/or outputting the combined score to a user for enabling the user to determine the biomedical state of the tissue sample.

A "relative distribution" as used herein is a function that is descriptive of the spatial dispersion between two types of objects. According to preferred embodiments, a "relative distribution" is a function that captures the distances of objects of a first type to objects of a second type. According to preferred embodiments, a "relative distribution" quantifies the spatial dispersion in a way that is invariant to rotations and reflections. Several simple measures of spatial dispersion can be defined using e.g. a covariance matrix of the coordinates of the objects. The trace, the determinant, and the largest eigenvalue of the covariance matrix can be used as measures of spatial dispersion. An example of a measure of spatial dispersion that is not based on the covariance matrix is the average distance between nearest neighbors. A further and preferred measure of a spatial dispersion is Ripley's K function.

A "reference relative distribution" as used herein is a relative distribution that captures the degree of spatial dispersions between two types of objects (e.g. reference A-type cells and reference B-type cells) and that is used as a reference A "reference" is a kind of "standard" or "baseline" against which another information, e.g. another relative distribution of the two types of objects, can be compared. The reference relative distribution may be derived by means of computational simulation based on an expected distribution of objects, e.g. based on a Poisson distribution, or may be derived empirically from a relative distribution of objects observed in one or more reference samples. The reference relative distribution can represent a "baseline". It allows comparing the relative distribution of different cell types in a currently examined tissue sample with the relative distribution of the same types of cells in one or more reference tissue samples having a known biomedical state. The comparison of an observed relative distribution with a reference relative distribution may allow determining if the relative distribution of cells in a tissue sample significantly deviates from the relative distribution of said types of cells in a simulated or empirically determined reference relative distribution.

An "observed relative distribution" as used herein is a relative distribution that captures the degree of spatial dispersions between two types of objects (e.g. two types of cells) that within a tissue sample depicted in a currently analyzed digital image.

A "proximity score" as used herein is a score value computed as a function of the observed relative distribution and the reference relative distribution. Preferably, the proximity score is computed by computing the difference between one or more distances or distance measures encoded in the observed relative distribution and the reference relative distribution. According to embodiments of the invention, the score value is a numerical data value. According to embodiments of the invention, the score value is computed as the difference (delta) between the reference distribution and the observed distribution. For example, the score value can be computed as the differences of two distances r1, r2, wherein r1 can be the distance from an A-type cell within which on average a particular number of B-type cells is observed according to the observed relative distribution and wherein r2 can be the distance from a (simulated or empirically determined) A-type cell within which on average a particular number of (simulated or empirically determined) B-type cells is observed according to the reference relative distribution. Alternatively, the difference can be the difference of two areas whereby one area is defined by two predefined distance thresholds, a baseline for "0 observed occurrences" and a section of the reference relative distribution curve between the two distance thresholds, and the second area is defined by the two predefined distance thresholds, the baseline and a section of the observed relative distribution curve between the two distance thresholds.

The "tumor-immunophenotyping" or "spatial immune infiltration phenotyping" as used herein is a method to separate tumors into different groups or to map them on a continuous or discrete spectrum based on the grade of inflammation in the tumor. The extremes of the spectrum would represent tumors highly inflamed versus tumor tissue completely devoid of immune cells.

The "Ripley's K" as used herein is a spatial descriptive statistics that can be used for generating the reference relative distribution and/or the observed relative distribution. To be more particular, it is a measure of spatial dispersion between two types of objects. Ripley's K function has been described e.g. by Philip M. Dixon, Volume 3, pp 1796-1803 in Encyclopedia of Environmetrics (ISBN 0471 899976) Edited by Abdel H. El-Shaarawi and Walter W. Piegorsch, John Wiley & Sons, Ltd, Chichester, 2002. Ripley's K(t) function, also referred to as the "K-function" or "Ripley's K", is a mathematical representation of the expected value of the distances between cells of the A-type and cells of the B-type.

A "biomedical state" as used herein is any disease-, metabolism-, genome-, proteome-, related or morphological state of a tissue that is known of or predictive or therapeutic use in the context of biology and/or medicine. For example, the "biomedical state" of a tissue can relate to the degree of infiltration of a tumor tissue by immune cells, it can relate to the degree of differentiation of a tumor tissue or of a tissue of a young, developing organism.

BRIEF DESCRIPTION OF THE DRAWINGS

In the following embodiments of the invention are explained in greater detail, by way of example only, making reference to the drawings in which:

DETAILED DESCRIPTION

Figure 1:
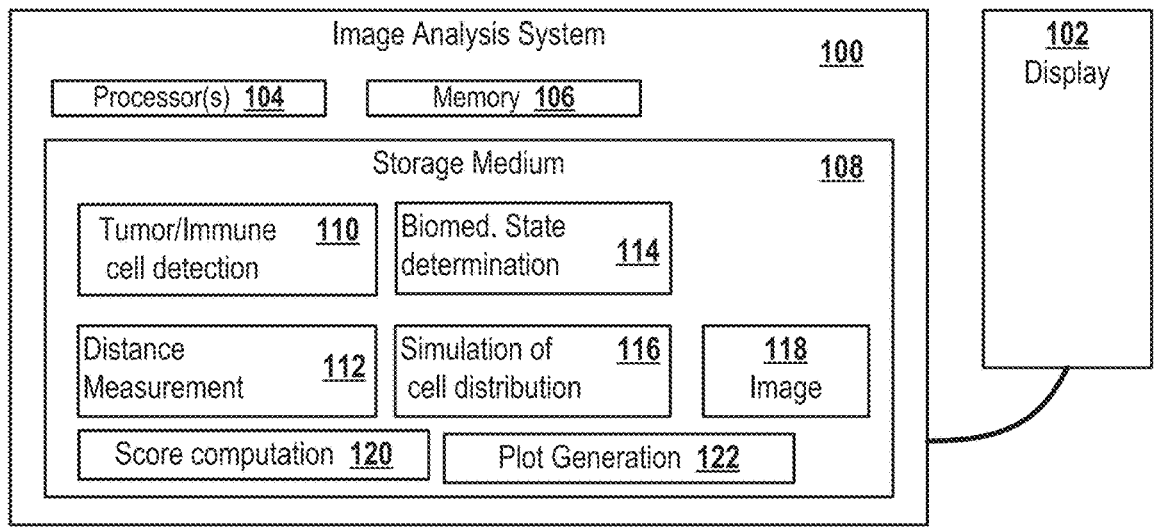
Figure 2:
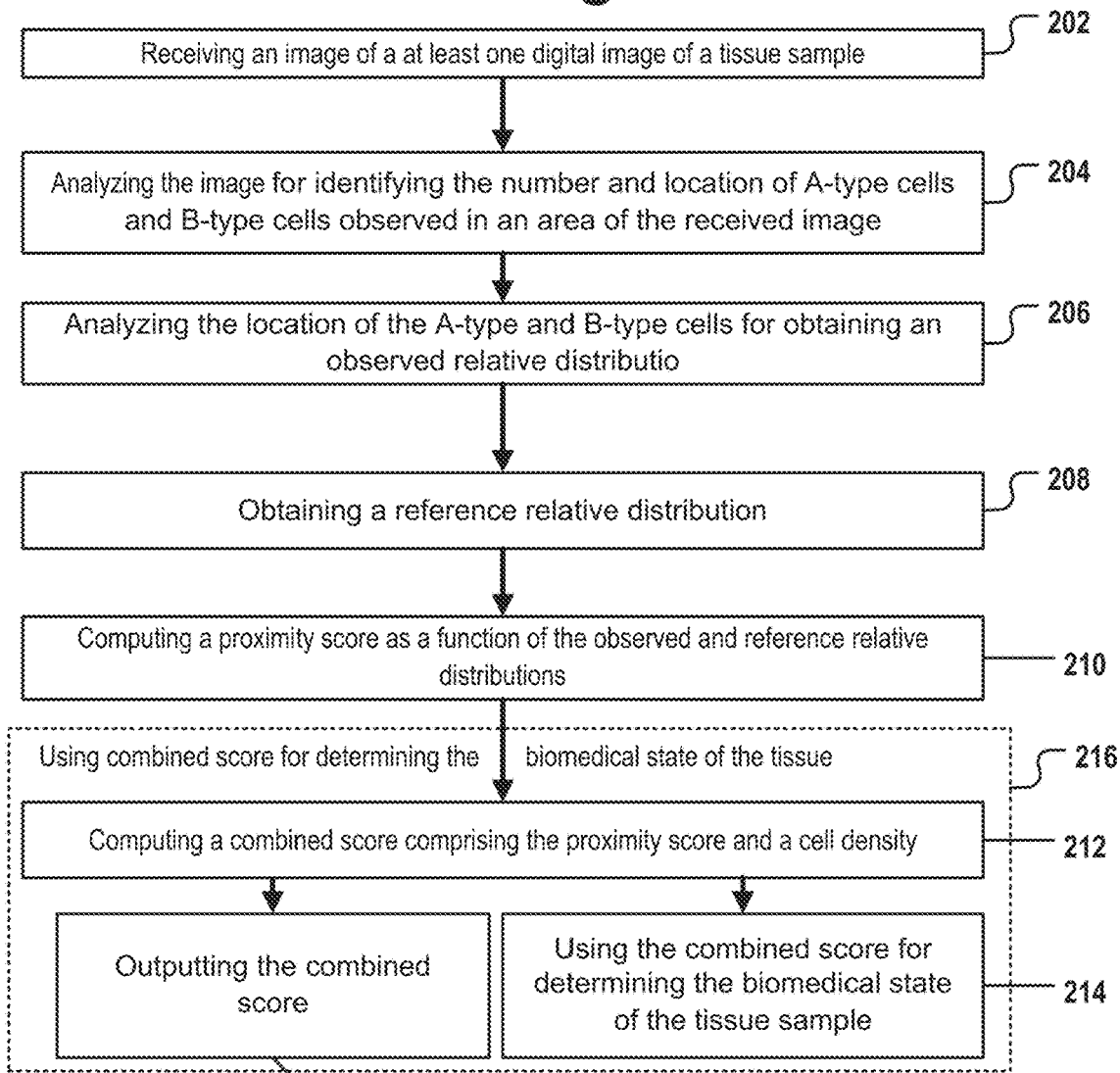
Figure 3:
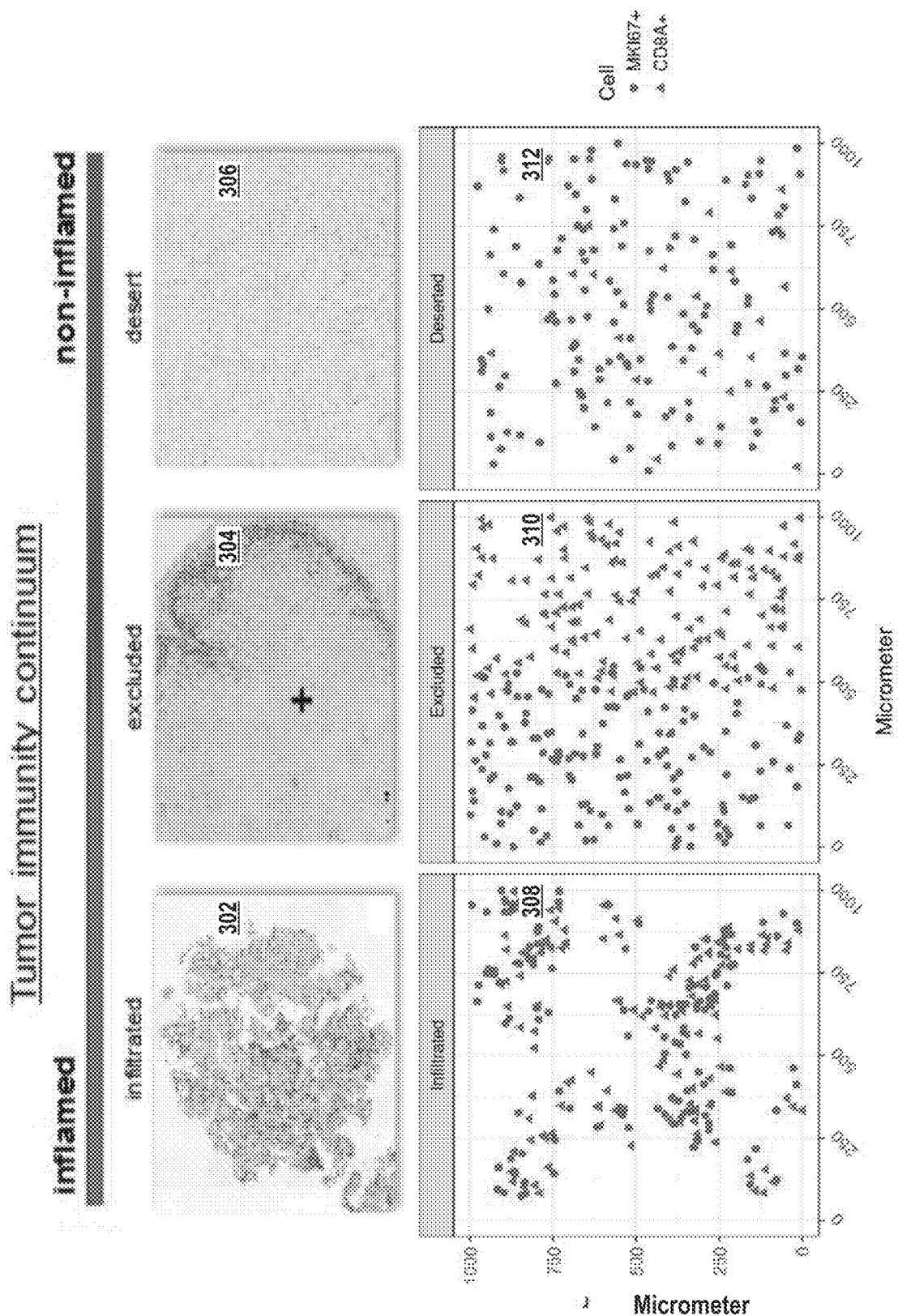
Figure 4:
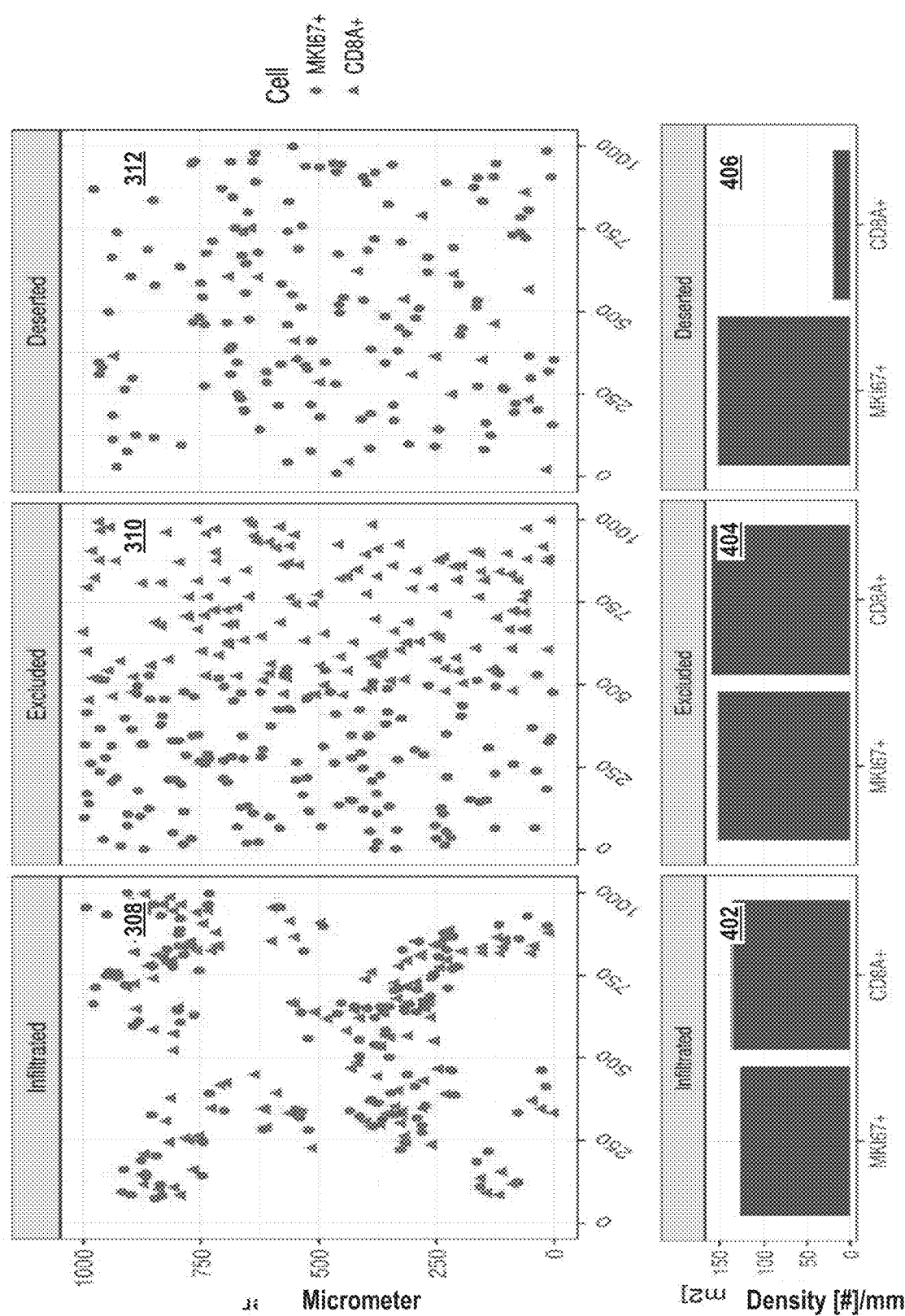
Figure 5:
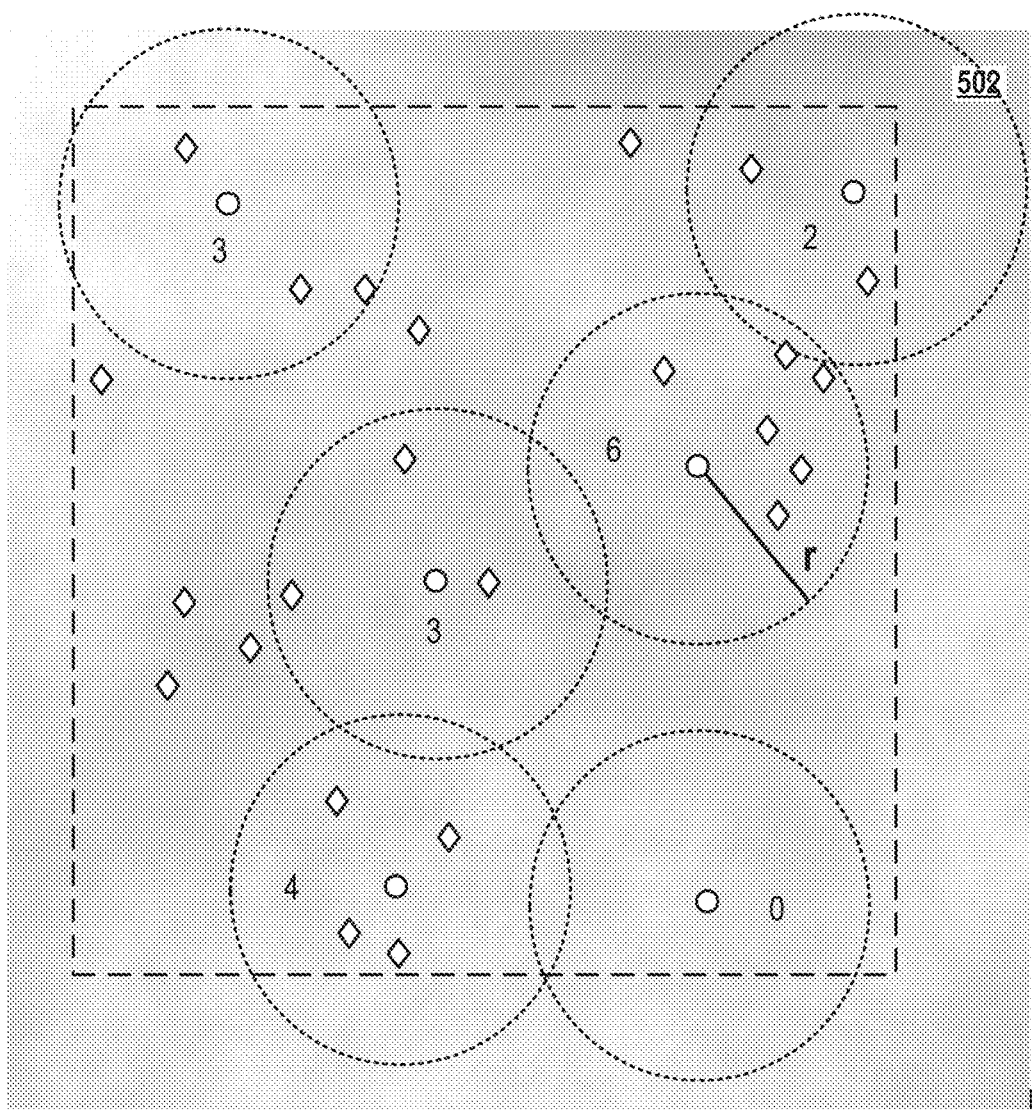
Figure 6:
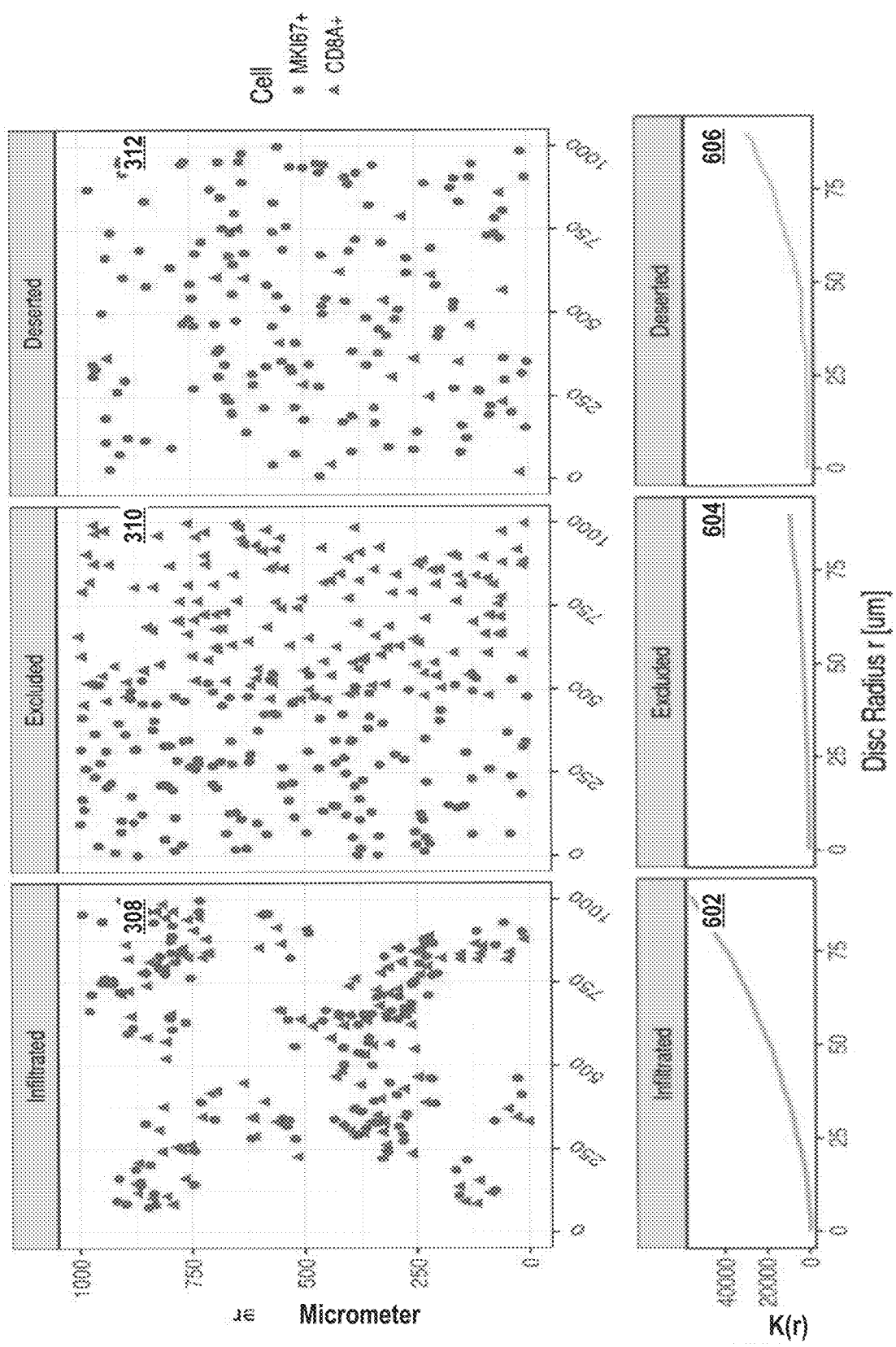
Figure 10:
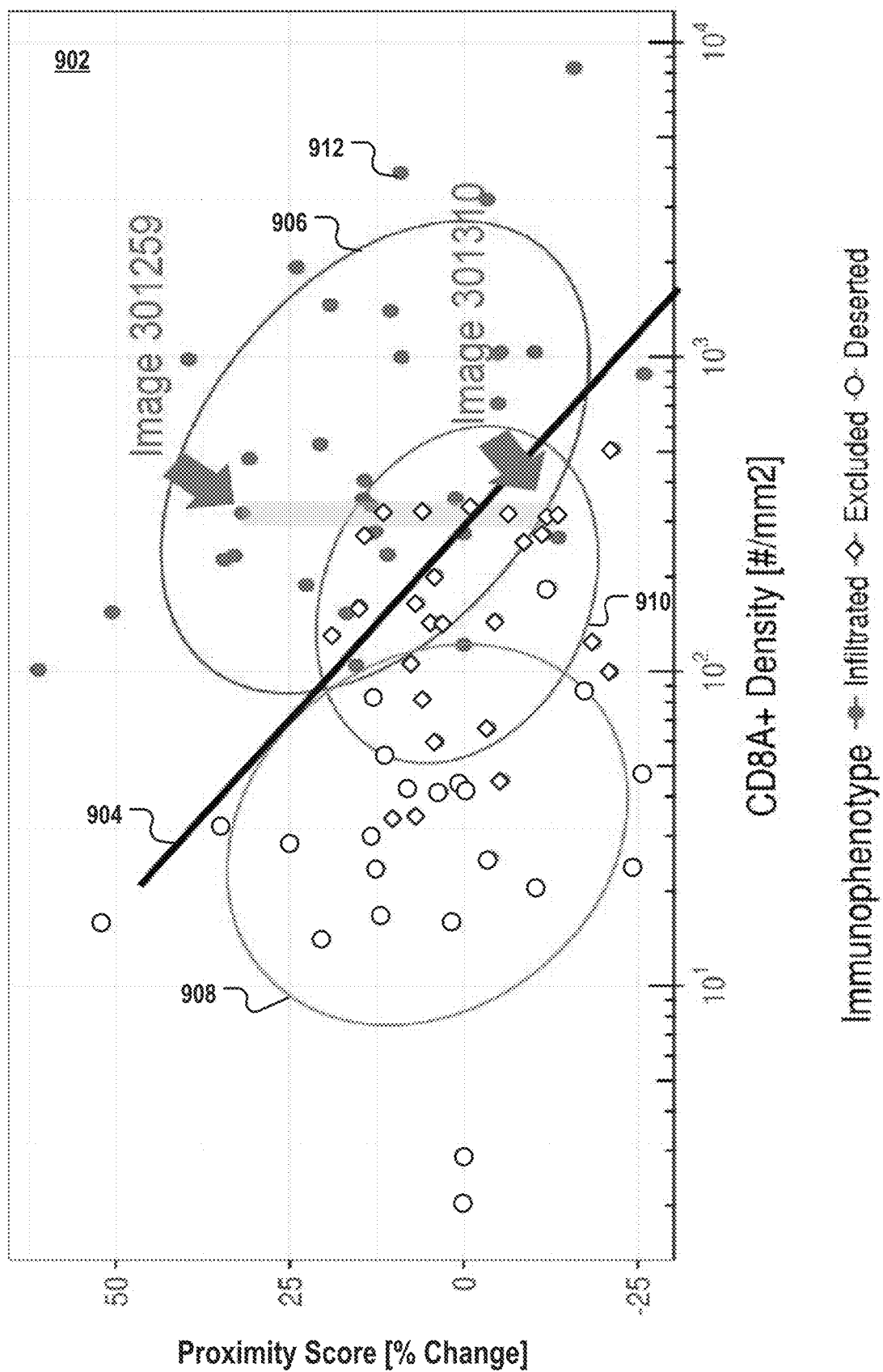
Figure 11:
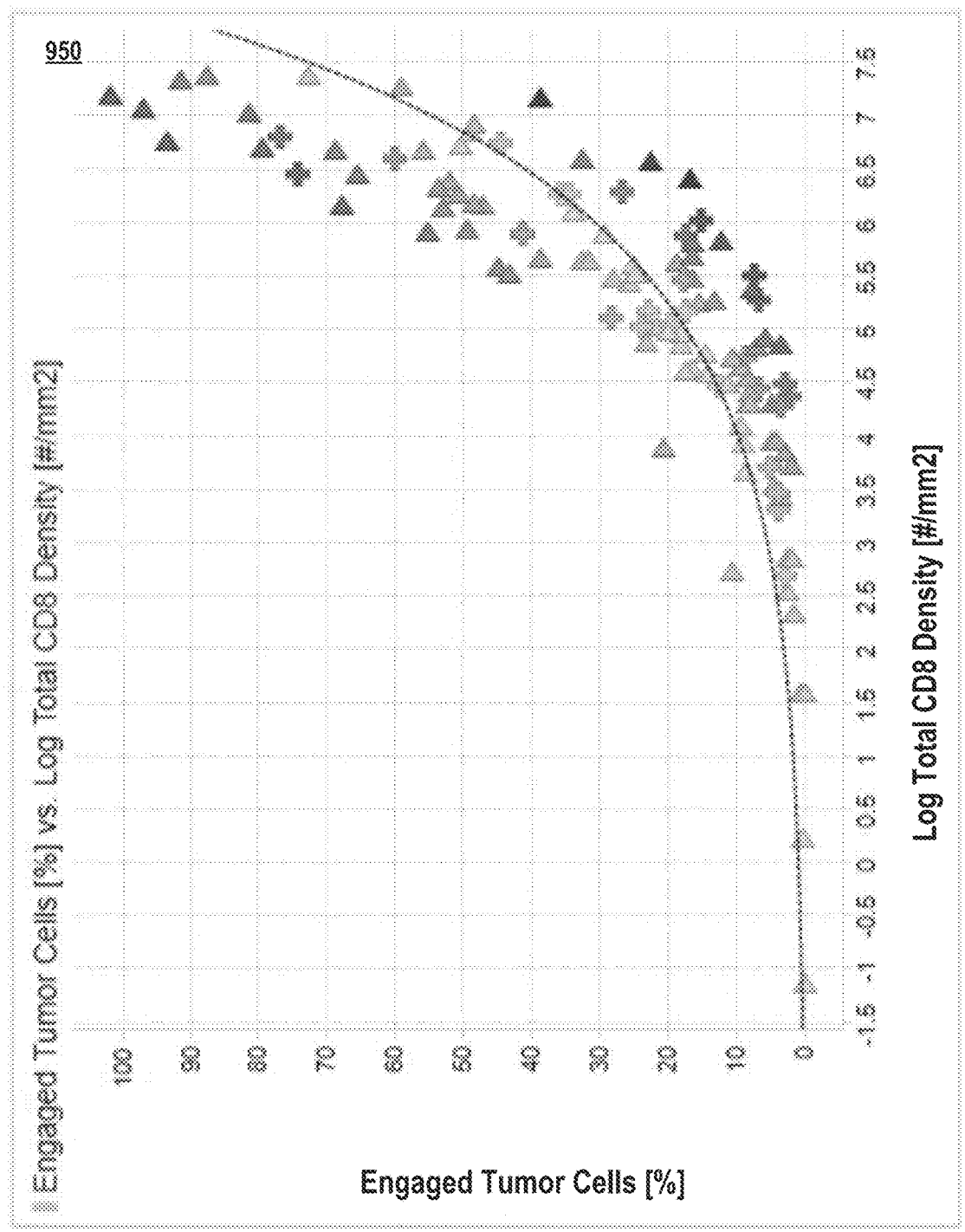
Figure 12:
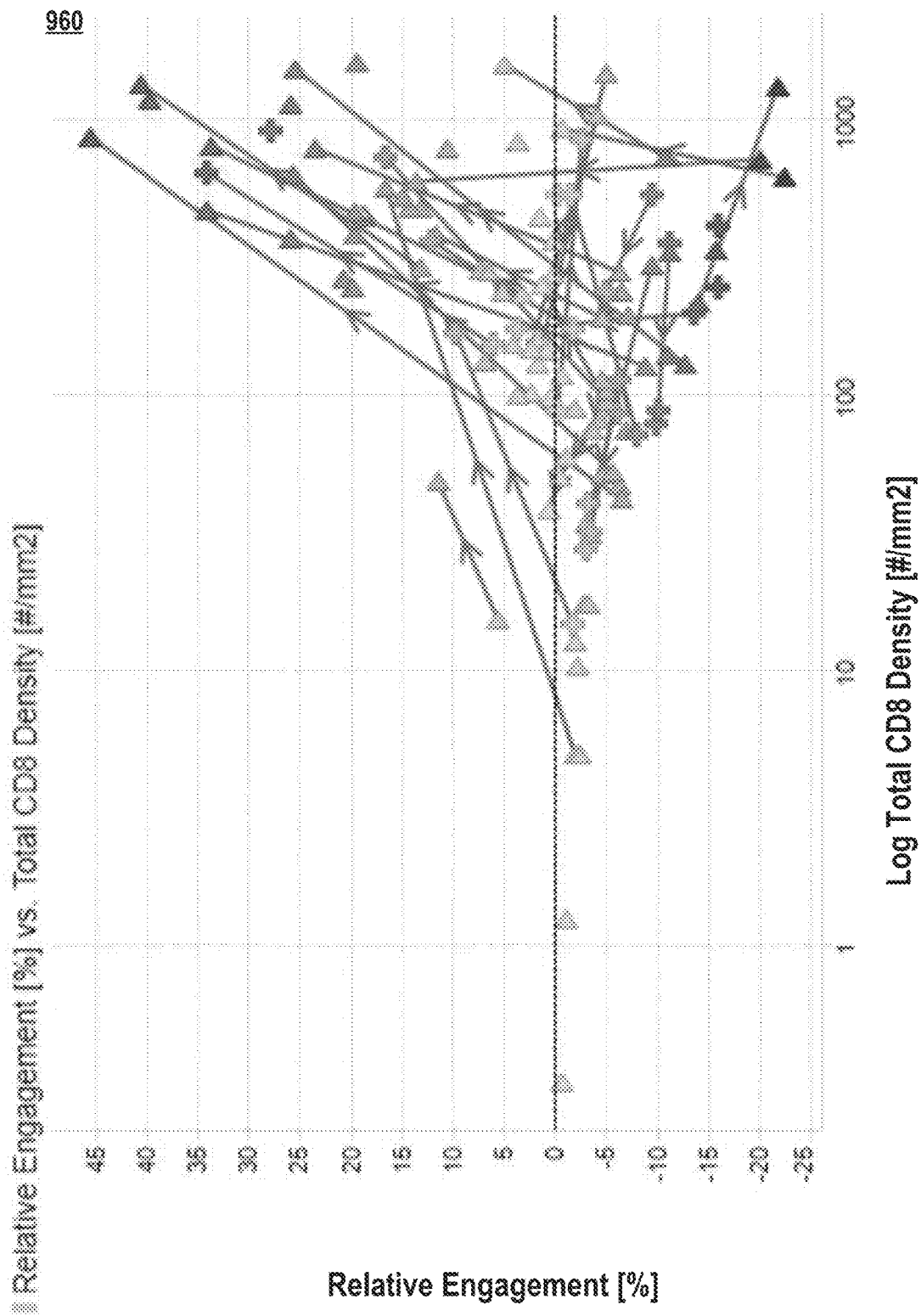
Figure 13:
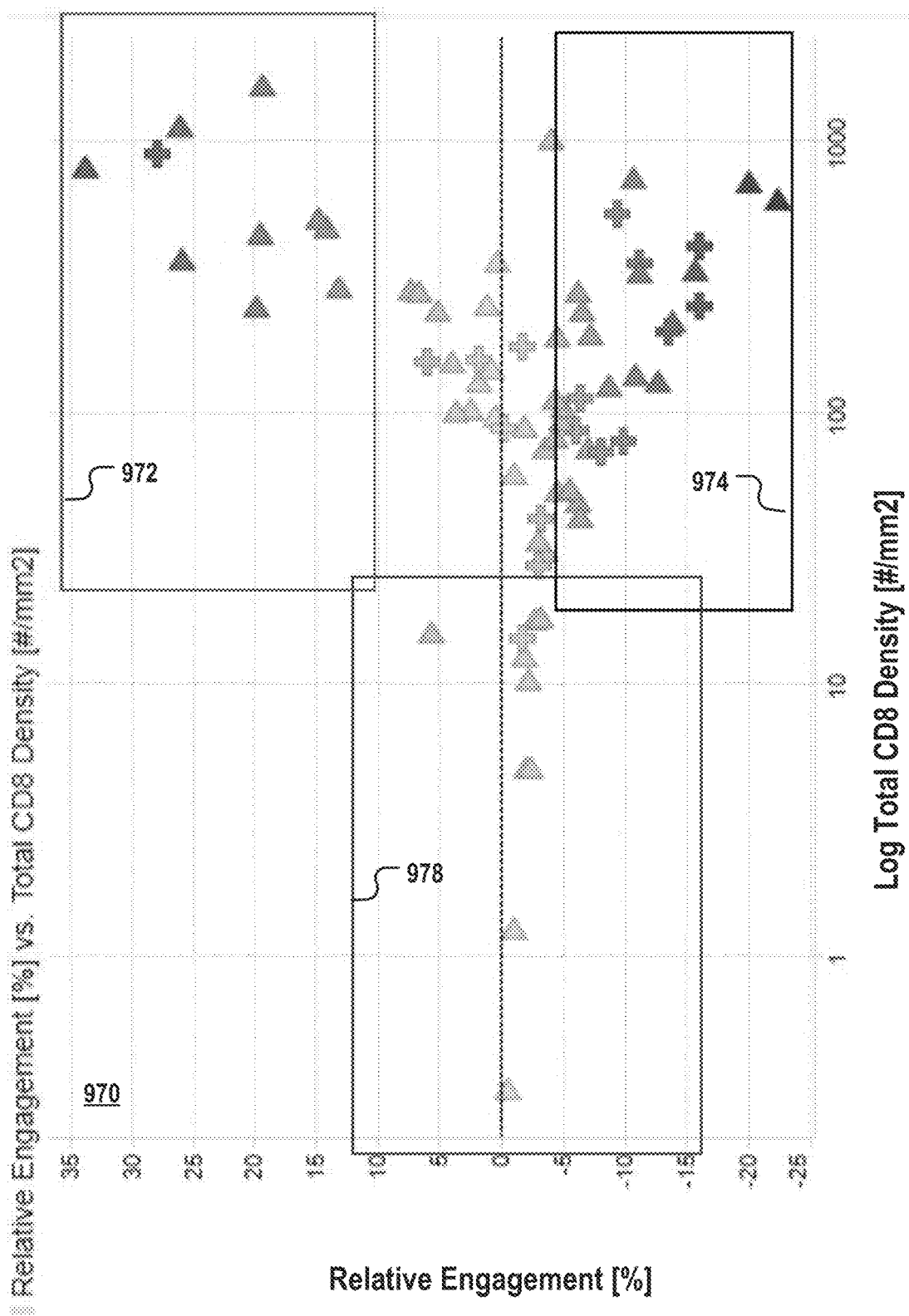
Figure 14:
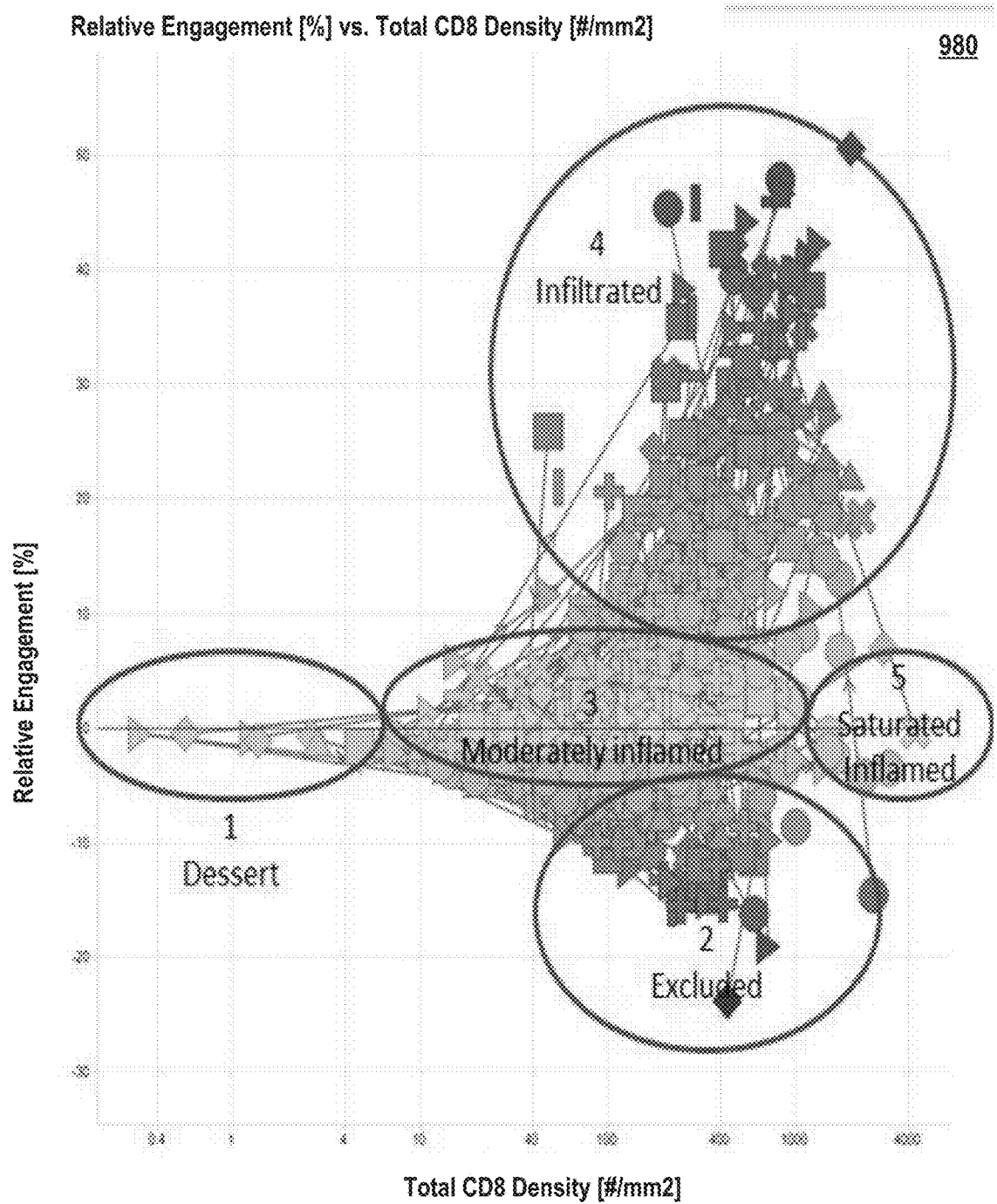

FIG. 1 is a block diagram of an image analysis system;
FIG. 2 is a flow chart of an image analysis method for determining the biomedical state of a tissue sample;
FIG. 3 depicts images of three tumor tissue samples having different degrees of infiltration with immune cells and respective schematic illustrations of the cell distributions;
FIG. 4 depicts the immune cell and tumor cell densities in the three tissue samples of FIG. 3, respectively;
FIG. 5 depicts the use of radii for defining a spatial cell neighborhood and for computing relative distributions of cells of different cell types;
FIG. 6 depicts the observed relative distributions obtained from the images showing the "infiltrated" and the "excluded" infiltration state;
FIG. 7 depicts two 2D plots respectively comprising an observed relative distribution, a reference relative distribution, a confidence belt and a "delta" used as the proximity score;
FIG. 8 depicts an alternative, area-based analysis of a 2D plot for determining a "delta" to be used as proximity score;
FIG. 9 depicts fluorescent images of two tumor tissue samples having either "excluded" or "infiltrated" immune cell infiltration status;
FIG. 10 depicts a 2D score plot comprising clusters of combined scores, each combined score representing a respective one of a plurality of different tissue samples;
FIG. 11 depicts a logarithmic 2D score plot comprising points representing combined score values obtained from a plurality of patients;
FIG. 12 depicts a logarithmic 2D score plot comprising pairwise connected points representing combined score values obtained from a plurality of patients before and after treatment;
FIG. 13 depicts a logarithmic 2D score plot comprising three clusters of combined score values obtained from a plurality of patients; and
FIG. 14 depicts a logarithmic 2D score plot comprising five clusters of combined score values obtained from a plurality of patients.

FIG. 1 is a block diagram of an image analysis system 100 according to an embodiment of the invention. The system comprises one or more processors 104, a main memory 106 and a non-volatile storage medium 108. The storage medium comprises one or more application programs or modules 110, 114, 112, 116, 120, 122 configured for performing one or more data processing tasks such as the automated detection of cells of different cell types (module 110), the measuring of cell-cell distances (module 112), the simulation of cell distributions of a given density (module 116), the plotting of various scores and curves (module 122), the computation of proximity scores and combined scores (module 120) and the automated determination or prediction of a biomedical state of a tissue sample based on the combined score (module 114). The various modules can be combined arbitrarily in one or more application programs. For example, the functionality provided by or modules can be combined into a single application program. Alternatively, some functionalities can be performed by separate application programs. For example, the simulation of a given distribution can be performed by mathematical programs such as R, the computation of distances can be performed by or in interaction with a spatial DBMS, and the identification of cells of a particular cell type can be implemented by a digital pathology image analysis software.

The storage medium 108, e.g. an electromagnetic hard disk drive, can comprise one or more digital pathology images 118 respectively depicting a tissue sample. For example, the digital image 118 can be a monochrome image or a multichannel image. For example, the image 118 can be an RGB image. The image 118 can be a brightfield microscopy image or a fluorescence image. Typically, the image is a multichannel image obtained by fluorescence microscopy from a tissue sample having been stained with one or more biomarker specific stains having different colors.

The cell type detection module can be configured for automatically detecting tumor cells and immune cells and for storing the locations and types of the automatically detected cells in a spatial database. The identification of cells and respective cell types may perform a connected component analysis and edge detection routines in order to identify pixel blobs representing cells. Information encoded in the color or other image features can be used for identifying the cell type. The color information encoded in the digital image 118 is typically indicative of a particular biomarker or a particular set of biomarkers. For example, a specific set of cytokeratins may be stained with suitable antibodies which are coupled to a fluorescent or colored dye. Multiple monochromatic images 118 can be derived from a multi-spectral fluorescent image of a particular tissue sample by applying a color deconvolution algorithm.

For example, cells expressing a specific tumor marker or a proliferation marker which do not express an immune cell specific marker can be considered as tumor cells. Cells expressing immune cell specific markers such as CD8A can be identified as immune cells.

According to another example, primary antibody Anti-Pan Keratin "AE1/AE3/PCK26" of Ventana Medical Systems, Inc. can be used to stain poorly differentiated malignant tumors. A set of anti-Pan Keratin antibodies "AE1/AE3/PCK26" specifically binds to antigens located in the cytoplasm of simple and complex epithelial cells. It is a mouse monoclonal antibody cocktail raised against an epitope found on human epidermal keratins as reported by Woodcock-Mitchell, et al. This antibody cocktail reacts with the 56.5 kD, 50 kD, 50'kD, 48 kD, and 40 kD cytokeratins of the acidic subfamily and 65-67 kD, 64 kD, 59 kD, 58 kD, 56 kD, and 52 kD cytokeratins of the basic subfamily.

According to embodiments, the one or more digital images 118 are generated by a color deconvolution algorithm or are stored directly in the storage medium after their acquisition by a camera or other image capturing device. The image analysis system can optionally comprise an image capture device, e.g. a camera (not shown).

Moreover, the system 100 is coupled to or comprises a display 102, e.g. an LCD display. The system uses the display 102 for displaying the digital images 118 of tissue samples of various patients, for displaying various plots comprising densities, relative distributions and combined score values and/or for displaying results of cluster analyses are biomedical tissue states having been identified automatically by on the combined score obtained from a particular tissue sample.

FIG. 2 is a flow chart of an image analysis method for determining the biomedical state of a tissue sample. The method will be described in the following using tumor cells and immune cells as examples for different cell types and using the immune cell infiltration state of a tumor tissue sample as the biomedical tissue state to be automatically determined. The method may allow automatically stratifying patients in regards to potential response to cancer immune therapies using image analysis with spatial information. However, this is only one example of how the computation of a combined score as described herein from the relative distribution of two different cell types can be used in the context of biology and medicine for quickly, automatically and accurately determining the biomedical state of a particular tissue. Differences in the distribution of two cell types from an expected reference distribution may be used for the determination and sub-classification of many other diseases or physiological states and/or for identifying an appropriate treatment mode or drug.

The method can be implemented in and performed for example by an image analysis system 100 as depicted in FIG. 1. In a first step 202, the image analysis system 100 receives a digital image of a tissue sample. For example, the digital image can be directly received from an image capturing device, e.g. a microscope, can be received via a network, e.g. the Internet, or can be read from a non-volatile storage medium 108.

Next in step 204, the image analysis system analyzes the received image for identifying the number and location of A-type cells (e.g. tumor cells) and B-type cells (e.g. immune cells) observed in an area of the received image. The image analysis can comprise the application of various image processing and analysis techniques such as color deconvolution, image segmentation, blob detection, connected component analysis, feature extraction, future clustering and the like.

Next in step 206, the image analysis system analyzes the location of the A-type and B-type cells in the area for obtaining an observed relative distribution. The observed relative distribution is indicative of observed distances between the A-type cells and the B-type cells in the area. In addition, the image analysis system determines the densities of the observed tumor cells and immune cells in the image area, respectively.

Next in step 208, the image analysis system obtains a reference relative distribution. The reference relative distribution can be obtained, for example, by performing a plurality of simulations for generating expected distributions of tumor cells and immune cells, respectively, and determining the distances between the different types of simulated cells. The expected distributions can be, in particular, random distributions, e.g. a Poisson distribution assuming the same densities of tumor cells and immune cells as observed in the image area.

Next in step 210, a proximity score is computed as a difference of the reference relative distribution and the observed relative distribution. The expression "computing a difference between a reference relative distribution and an observed relative distribution" as used herein means that the proximity score is computed as a function of the observed and relative distributions, whereby the function comprises at least one operation that computes the difference between one or more "observed" distances encoded in the observed relative distribution and one or more "reference" distances encoded in the reference relative distribution.

Next in step 212, the image analysis system combines the proximity score with the density of immune cells measured in the received digital image 118 for providing a "combined score".

Next in step 214, the image analysis system uses the combined score for automatically determining the biomedical state of the tissue sample, e.g. a particular infiltration state. In addition, or alternatively, the image analysis system displays in step 216 the combined score obtained for the tissue sample on a display 102 of the image analysis system to a user. Thereby, the user is enabled to visually assess the current biomedical state of the tissue and make according conclusions regarding the progress of the disease and suitable treatment options. For example, the combined score of the tissue sample can be represented as a data point in a 2-D score plot as depicted in FIGS. 9, 10-13.

According to preferred embodiments, the observed relative distribution and the reference relative distribution are computed using Ripley's K function.

According to alternative embodiments, a more simple approach can also be used. For example, the image analysis system 100 can receive 202 a digital image 118 of a tissue sample. The image analysis system analyzes 204 the received image and identifies CD8+ immune cells and Ki-67+ tumor cells in the image or in a particular sub-area of the image. For example, the sub-area may be an image tile of predefined size or may be an automatically detected tumor tissue region. For each of the identified tumor cells, the image analysis system determines 206 the distance of that tumor cells to its nearest immune cell. After the distances of all tumor cells to their respectively nearest immune cells have been determined, the totality of distances may correspond to and represent a "observed relative distribution" of tumor cells and immune cells in the tissue. In the next step, the identified density of tumor cells and immune cells in the image or in the tumor tissue area is determined and used for simulating a Poisson distribution of simulated tumor cells and simulated immune cells, respectively. Thereby, the density of the simulated tumor cells and simulated immune cells is identical to the observed density of tumor cells and immune cells in the tissue. Then, the distances of all simulated tumor cells to their respectively nearest simulated immune cell are determined 208 and represented as a "reference relative distribution". Then, the proximity score is computed 210 a function of the determined distances. For example, the distance where—on average—every tumor cell comprises one immune cell in its neighborhood can be determined both for the observed relative distribution and for the reference relative distribution and the difference of these two differences can be used as the proximity score. Then, the image analysis system provides 212 a combined score comprising the proximity score and the immune cell density observed in the image 118 and uses 214 the combined score either for automatically determining the biomedical state (e.g. infiltration state) of the tissue and/or for displaying 216 the combined score on a 2-D score plot as depicted, for example, in FIGS. 9, 10-13 on a display 102 of the image analysis system for enabling a user to visually assess the current biomedical state of the tissue sample.

FIG. 3 depicts images of three tumor tissue samples having different degrees of infiltration with immune cells and respective schematic illustrations of the cell distributions.

Image 302 depicts a digital pathology image of tumor tissue having "infiltrated" state, meaning that the tumor tissue is heavily infiltrated with immune cells. The relative spatial distribution of immune cells (triangles) and tumor cells (dots) in "infiltrated" tumor tissue is illustrated in the schematic drawing 308 below.

Image 304 depicts a digital pathology image of tumor tissue having "excluded" state, meaning that the tumor has created a kind of "boundary" that prevents the immune cells form immigrating into the tumor tissue. The relative spatial distribution of immune cells and tumor cells in "excluded" tumor tissue is illustrated in the schematic drawing 310 below.

Image 306 depicts a digital pathology image of tumor tissue having "deserted"/"desired" state, meaning that the tumor is basically free of any immune cells. The relative spatial distribution of immune cells and tumor cells and "deserted" tumor tissue is illustrated in the schematic drawing 312 below.

The depicted three images and distributions are unambiguous representatives of the above mentioned three different biomedical states. However, in most of the cases, the tissue samples are somewhere in between two different states. As a consequence, it is not possible with the currently available methods to provide for a reliable, objective and reproducible way of determining the biomedical state of a tissue sample that does not clearly fall into one of the three categories.

FIG. 4 depicts the immune cell and tumor cell densities in the three tissue samples of FIG. 3, respectively. In addition, FIG. 4 comprises plots 402, 404, 406 illustrating the immune cell densities (CD8A+) and tumor cell densities (Ki-67+) of the respective states. The figure shows that immune cell density is an important prognostic parameter for distinguishing "deserted" tissue from the other two tissue types, but is insufficient for distinguishing "infiltrated" from "excluded" tissue samples.

FIG. 5 depicts the use of radii for defining a spatial cell neighborhood and for computing relative distributions of cells of different cell types. The image depicts six tumor cells 504 indicated by a small circle and a plurality of immune cells indicated by small triangles. In order to obtain the observed relative distribution between immune cells and tumor cells in the image, each identified tumor cell is used as a center of a circle having radius r. The radius r defines a circular neighborhood. By a stepwise increasing the radius of the circle around the tumor cells, and by counting the number of immune cells contained in the respectively created circles, a cumulative measure of the number of immune cells in the surroundings of tumor cells can be obtained. The number of steps and respective radii can be chosen freely as a compromise between computational resource consumption and accuracy. For example, each step may increase the radius by 1 μm, or 5 μm, or 10 μm, etc. The association of the respective radii and the number of immune cells counted in the circular neighborhoods defined by the radii can be represented by various different mathematical formulas and distributions. Preferably, Ripley's K function is used for describing the relative spatial distribution of immune cells and tumor cells obtained by the stepwise increasing of the radii.

FIG. 6 depicts the observed relative distributions obtained from the images showing the "infiltrated" and the "excluded" infiltration state. The upper part of FIG. 6 depicts the schemes of the spatial distributions of immune cells and tumor cells depicted and described already in FIG. 3. The lower part of FIG. 6 depicts plots 602, 604, 606 respectively having a y-axis representing the result of the Ripley's K function K(r) and an x-axis representing the (stepwise increased) radius. In the depicted example, the radius is increased by 1 μm. Hence, one data point is obtained for every micrometer in the x-axis. The curves in the plot are obtained by curve fitting of the obtained data points in the plot. As can be seen in the infiltrated case, the result obtained by the Ripley's K function positively correlates with the increase of the radius r. However, in the "excluded" case, there is almost no increase of K(r) with increasing r. In the "deserted" case, there is a slight increase of K(r) with increasing r. Hence, the relative spatial distribution may not always be sufficient for distinguishing and excluded from a deserted state, but can clearly distinguish and infiltrated state from an excluded or deserted state. Hence, a combination of the proximity score encoding differences in the relative spatial distributions and the density information may allow clearly identifying the current biomedical state of the tissue within a complex continuum of states.

FIG. 7A depicts a 2D plot 702 whose y-axis represents the number of immune cells observed in a circular neighborhood around a tumor cell defined by the circle radius r and whose x-axis represents the radius r.

The first plot 702 depicts the observed average number of immune cells within a circle of radius r around tumor cells for different radii in a tissue sample having "infiltrated" state. The curve 706 represents an observed relative distribution was obtained by curve fitting of the respective data points in the plot 702.

The second plot 704 depicts the observed average number of immune cells within a circle of radius r around tumor cells for different radii in a tissue sample having "excluded" state. The curve 708 represents an observed relative distribution and was obtained by curve fitting of the respective data points in the plot 704.

Figure 7B:
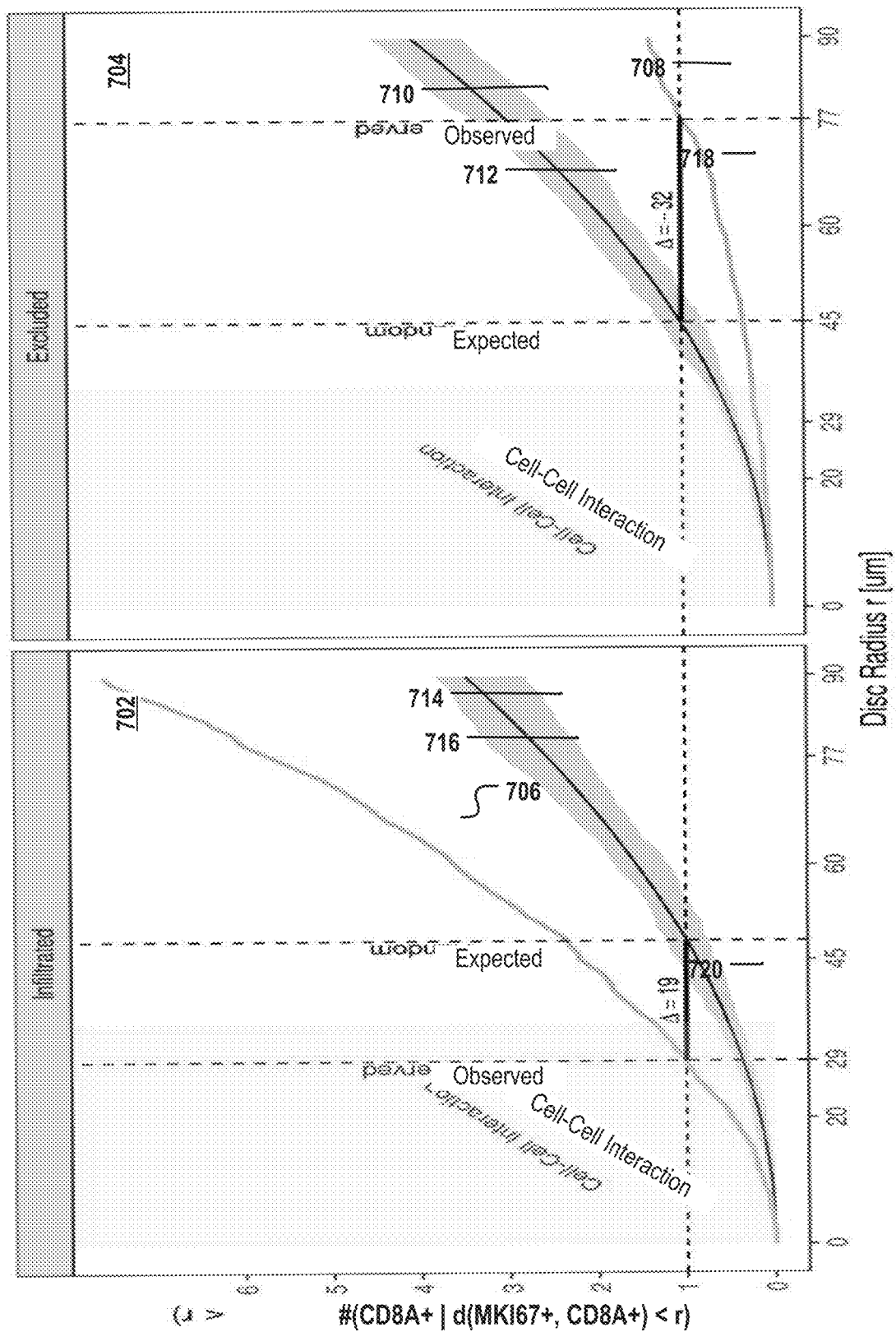
Figure 8:
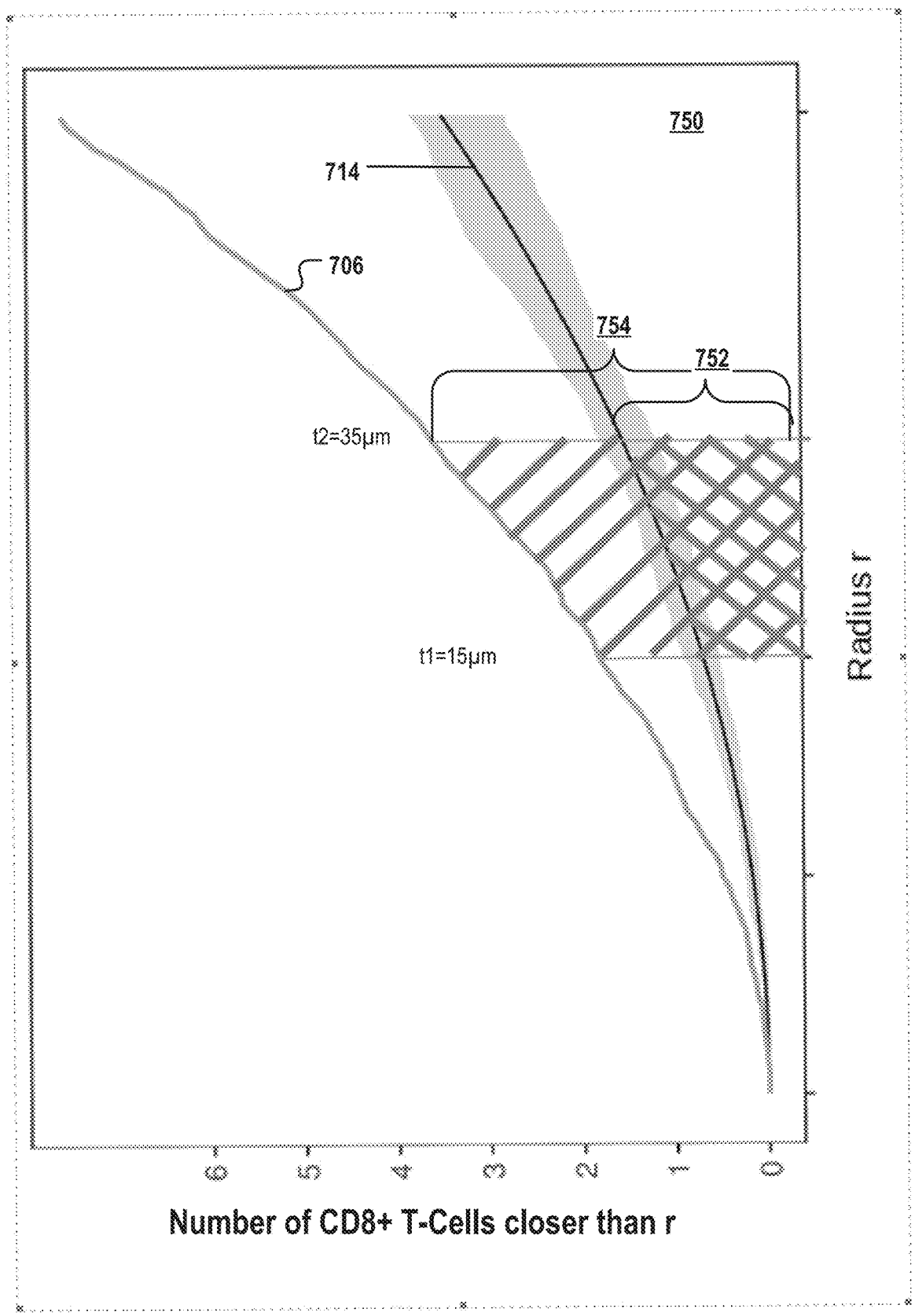

FIG. 7B depicts the 2D plots 702, 704 having been supplemented with additional information.

Plot 702 was supplemented by an average reference relative distribution 714. The average reference relative distribution was obtained by generating a plurality (e.g. 40) of initial reference relative distributions. Each initial relative distribution is computed by simulating a Poisson distribution of simulated tumor cells having the same cell density as the observed tumor cells, by simulating a Poisson distribution of simulated immune cells having the same cell density as the observed immune cells, and determining a distance measure (e.g. the number of immune cells obtained in the circular neighborhood of tumor cells using radius r) that provides information on the relative spatial distribution of immune cells and tumor cells. For each of the examined radii (r=1 μm, 2 μm, . . . , 98 μm, 99 μm, 100 μm), and for each of the 40 simulations, the average number of immune cells in a circle of radius r around a tumor cell is determined. Then, for each of the examined radii, the minimum, mean and maximum number of immune cells in a circle of radius r around a tumor cell is determined. The mean number is plotted as a data point for each r for generating a curve 714 based on curve fitting. The curve 714 represents the simulation-based reference relative distribution. The minimum number is plotted as a data point for each r for generating the lower border of the confidence belt 716 by curve fitting of said data points. The maximum number is plotted as a data point for each r for generating the upper border of the confidence belt 716 by curve fitting of said data points. The confidence belt 716 represents a region within which any observed relative distribution is assumed to be not significantly different from the reference relative distribution 714.

The "delta=19" is the proximity score obtained by identifying a first point RP in the reference relative distribution 714 where the average number of immune cells in the circular tumor cell environment is "1", identifying a second point OP in the observed relative distribution 706 where the average number of immune cells in the circular tumor cell environment is "1", and subtracting the x-values (radii) of the first and second points. The resulting difference ("delta of radii" or "delta of distances") is used as the proximity score of a tissue sample. A user can easily infer from the fact that the second point OP lies outside of the confidence belt 716 that the observed relative distribution 706 is significantly different from the expected/reference relative distribution 714.

Plot 704 was supplemented by an average reference relative distribution 710. The average reference relative distribution was obtained by generating a plurality (e.g. 40) of initial reference relative distributions. Each initial relative distribution is computed by simulating a Poisson distribution of simulated tumor cells having the same cell density as the observed tumor cells of the tissue represented in plot 704 as described above for the plot 702. The curve 710 represents the simulation-based reference relative distribution. The minimum number is plotted as a data point for each r for generating the lower border of the confidence belt 712 by curve fitting of said data points. The maximum number is plotted as a data point for each r for generating the upper border of the confidence belt 712 by curve fitting of said data points. The confidence belt 712 represents a region within which any observed relative distribution is assumed to be not significantly different from the reference relative distribution 710.

The "delta=32" is the proximity score obtained by identifying a first point RP in the reference relative distribution 710 where the average number of immune cells in the circular tumor cell environment is "1", identifying a second point OP in the observed relative distribution 708 where the average number of immune cells in the circular tumor cell environment is "1", and subtracting the x-values (radii) of the first and second points. The resulting difference ("delta of radii") is used as the proximity score of a tissue sample. A user can easily infer from the fact that the second point OP lies outside of the confidence belt 714 that the observed relative distribution 708 is significantly different from the expected/reference relative distribution 710.

FIG. 8 depicts a plot 750 that is a modified version of plot 702 depicted in FIG. 7B. Plot 750 can be used for automatically or manually determining an alternative, area-based "delta" to be used as proximity score.

Plot 750 shows an average reference relative distribution 714 and an observed relative distribution 706. In addition, plot 750 shows a first predefined distance threshold t1 having a value of e.g. 10-20 μm, in this example 15 μm, and a second predefined distance threshold t2 having a value of e.g. 30-40 μm, in this example 35 μm. The two thresholds t1, t2 respectively correspond to an auxiliary line.

The two auxiliary lines corresponding to t1 and t2, the base line for "number of CD8 #T-Cells <r=0" and the observed relative distribution curve 706 define a first area that is graphically represented by the "///" hatching. For example, the vertical line 754 is the border of the first area defined by the second distance threshold t2.

The two auxiliary lines corresponding to t1 and t2, the base line for "number of CD8 #T-Cells <r=0" and the average reference relative distribution curve 714 define a second area that is graphically represented by the "\\\\"

hatching. For example, the vertical line 752 is the border of the second area defined by the second distance threshold t2.

The area where the first area and the second area overlap is indicated by crossed "XXX" hatching.

A "delta value" can now be computed as the difference or ratio of the size of the first and the second area. This "delta value", also referred to as "delta of area sizes", is used as the proximity score of a tissue sample. A user can easily infer from the positions of the curve section of curve 706 that lies far outside of the grey confidence belt surrounding curve 714 that the observed relative distribution 706 is significantly different from the reference relative distribution 714.

FIG. 9 depicts a fluorescent image 804 of a tumor tissue sample having infiltration state "excluded" and a fluorescent image 806 of a tumor tissue sample having infiltration state "infiltrated". Tumor samples from clinical trials were formalin fixed, cut into 2.5 μm thick sections and stained with a duplex chromogenic assay for CD8 and Ki-67. The stained slides were scanned and imported into a digital pathology platform for manual annotation by pathologists to identify tumor regions, normal tissue regions and necrotic regions. Areas with artifacts were excluded. The image underwent automated whole slide image analysis with a software logic adapted to automatically detect CD8-Ki-67 double positive cells, CD8 positive-Ki-67 negative T cells and Ki-67 positive and CD8 negative tumor cells. The detection was checked for accuracy by a pathologist before the results were entered into the database. Only objects detected in regions of tumor annotation was used for further analysis. Densities of the CD8+ T-cells, CD8+/Ki-67+ cells, CD8+/Ki-67− cells as well as CD8−/Ki-67+ tumor cells were calculated. Fluorescent images of this type can be used for stratifying patients as described in the following figures.

FIG. 10 depicts a 2D score plot comprising 80 combined scores clustered into three groups. Each combined score represents a respective one of 80 different patients from whom a tissue sample was taken.

The X axis of the 2-D score plot 902 represents the logarithm of the density of the immune cells (CD8A+ cells). The y-axis represents the proximity score. The cluster 906 represents tumor tissue that is "infiltrated" by immune cells. Cluster 908 represents tumor tissue determined to have the infiltration state "deserted". Cluster 910 represents tumor tissue determined to have the infiltration state "excluded". As can be inferred from the 2-D score plot, the immune cell density is an important parameter for distinguishing deserted from infiltrated tissue samples. However, the density alone may not be sufficient for distinguishing "excluded" tissue samples from "infiltrated" tissue samples. However, the additional dimension (y-axis) representing the proximity score "excluded" tumor samples from the "infiltrated" tumor samples.

The bold line 904 indicates that the combination of immune cell density and proximity score may allow for an improved separation of biomedical tissue states than the density information alone.

FIG. 11 depicts a logarithmic 2D score plot comprising points representing combined score values obtained from a plurality of patients. In general, it can be inferred that an increased immune cell density correlates with an increased engagement of immune cells and tumor cells. However, there are great differences between different patients and even between different tissue samples of the same patient. These differences may be used for determining the current biomedical state of the tissue and for identifying suitable treatment options.

FIG. 12 depicts a logarithmic 2D score plot comprising pair wise connected points representing combined score values obtained from a plurality of patients before and after treatment. The two data points connected by each arrow represent the combined score of a tissue sample obtained from a patient before the patient was treated with the drug and the combined score of another sample of the same patient obtained some days or weeks after the patient was treated with the drug. For example, the drug could be a drug that boosts the immune system. The drug could be a drug applied during immunotherapy of a patient.

It can be inferred from the plot that in response to the treatment of the patients with a particular drug, the engagement of immune cells and tumor cells was significantly increased in almost all patients (most of the arrows are pointing in upward direction in the plot). Moreover, the immune cell density increased in almost all patients in response to the application of the drug (most arrows are pointing from left to right). However, some few patients had no response or even showed a decrease of immune cell number and/or immune cell-tumor engagement.

Hence, obtaining a combined score from one or many patients repeatedly over the time may allow detecting trends in the progression of a disease or other physiological state. Often biology driven mechanisms are reflected in the tissue as a relative shift in the distribution of different cell types. Applicant has observed that the relative shift of distribution between tumor cells and immune cells, in addition to the density of the immune cells, provides meaningful information on a patient's location point on the elimination-equilibrium-escape balance of a tumor as well as an indication on the direction of the process over time, towards more elimination or more escape.

FIG. 13 depicts a logarithmic 2D score plot comprising combined score values obtained from a plurality of patients. The patients are grouped into three clusters based on the location of their respective combined score value in the plot. Hence, the combined score allows mapping the infiltration state of the tumor of a particular patient to a continuous scale representing different infiltration states of a tumor. The samples and patients can be grouped into three different clusters, but a more fine granular classification is also possible as revealed by FIG. 14. Cluster 972 represents the "infiltrated" state, cluster 974 represents the "excluded" state and cluster 976 represents the "desert" state.

FIG. 14 depicts a logarithmic 2D score plot comprising five clusters of combined score values obtained from a plurality of patients. In addition to the three different biomedical states represented by respective clusters in FIG. 13, FIG. 14 in addition comprises combined score clusters for the states "saturated inflamed" and "moderately inflamed".

The invention claimed is:

1. An image analysis method for determining the biomedical state of a tissue sample, the method being implemented by an image analysis system and comprising:
    receiving a digital image of a tissue sample;
    analyzing the received image for identifying the number and location of A-type cells and B-type cells observed in an area of the received image, wherein the A-type and the B-type are different cell types;
    analyzing the location of the A-type and B-type cells in the area for obtaining an observed relative distribution, the observed relative distribution being indicative of observed distances between the A-type cells and the B-type cells in the area;
    obtaining a reference relative distribution, the reference relative distribution being indicative of expected distances between reference A-type cells and reference B-type cells, wherein the expected distances are the distances that are expected assuming that the A-type cells and/or the B-type cells are distributed in the image area in accordance with a particular predefined mathematical distribution;

computing a proximity score as a difference of the reference relative distribution and the observed relative distribution;

computing a combined score, the combined score comprising the proximity score and comprising the density of the A-type cells and/or the density of the B-type cells;

using the combined score for determining the biomedical state of the tissue sample and/or outputting the combined score to a user for enabling the user to determine the biomedical state of the tissue sample.

2. The image analysis method of claim 1, the obtaining of the observed relative distribution comprising:
for each of the identified A-type cells observed in the image area:
a) selecting said A-type cell as a center of a circle with radius 0;
b) increasing the radius by one step for generating an increased cycle;
c) determining the number of B-type cells contained in the cycle generated in step b);
d) store the current radius of the circle in association with the number of B-type cells determined in step b) in a storage medium and repeat steps b), c) and d) until a termination criterion is reached
e) select an unselected one of the A-type cells and continue with a) using said newly selected A-type cell until all A-type cells have been selected;
provide the associated radii and numbers of observed B-type cells as the observed relative distribution.

3. The image analysis method of claim 1, wherein the observed relative distribution is computed as $K_{i,j}(r)$ or a derivative function of $K_{i,j}(r)$, wherein $K_{i,j}(r)$ is computed according to:

$$K_{i,j}(r) = \frac{1}{\lambda_i} E[t(u, r, X^j) \mid u \in X^{(i)}]$$

where $K_{i,j}(r)$ is a bivariate Ripley's K(t) function,
wherein i is an occurrence of object type "observed A-type cell";
wherein j is an occurrence of object type "observed B-type cell";
where $\lambda_j$ is the density (number per image area) of observed B-type cells;
where $X^i$ is the totality of observed A-type cells identified within the image area;
where $X^j$ is the totality of observed B-type cells identified within the image area;
where $u \in X^{(i)}$ is a cell being an observed A-type cell;
where r is a stepwise increased radius centered in an observed A-type cell;
wherein t is a function over u, r, and $X^j$ and counts the number of observed B-type cells within a circle of radius r around an observed A-type cell u in the image area;
where "$|u \in X^{(i)}$" means "over all u which are observed A-type cells";
where E is the expected value of t obtained over all u.

4. The method of claim 1, the obtaining of the reference relative distribution comprising:
computationally simulating a distribution of simulated reference A-type cells in the area, the number of simulated reference A-type cells being identical to the identified number of A-type cells observed in the image area;
computationally simulating a distribution of simulated reference B-type cells in the area, the number of simulated reference B-type cells being identical to the identified number of B-type cells observed in the image area;
computing the reference relative distribution as a function of the computationally simulated distributions of the reference A-type and reference B-type cells, the reference relative distribution being indicative of distances between the simulated reference A-type cells and the simulated reference B-type cells in the area.

5. The image analysis method of claim 4, the distribution of simulated reference A-type cells being a Poisson distribution and wherein the distribution of simulated reference B-type cells is a Poisson distribution.

6. The image analysis method of claim 4, computing the reference relative distribution as a function of the computationally simulated distributions of the reference A-type and reference B-type cells comprising:
for each of the randomly distributed simulated reference A-type cells:
a) selecting said simulated reference A-type cell as a center of a circle with radius 0;
b) increasing the radius by one step for generating an increased cycle;
c) determining the number of simulated reference B-type cells contained in the cycle generated in step b);
d) store the current radius of the circle in association with the number of simulated reference B-type cells determined in step b) in a storage medium and repeat steps b), c) and d) until a termination criterion is reached
e) select an unselected one of the simulated reference A-type cells and continue with a) using said newly selected simulated reference A-type cell until all simulated reference A-type cells have been selected;
provide the associated radii and numbers of simulated reference B-type cells as the reference relative distribution.

7. The image analysis method of claim 4, wherein the reference relative distribution is computed as $K_{i,j}(r)$ or a derivative function of $K_{i,j}(r)$, wherein $K_{i,j}(r)$ is computed according to:

$$K_{i,j}(r) = \frac{1}{\lambda_i} E[t(u, r, X^j) \mid u \in X^{(i)}]$$

where $K_{i,j}(r)$ is a bivariate Ripley's K(t) function,
wherein i is an occurrence of object type "observed A-type cell";
wherein j is an occurrence of object type "observed B-type cell";
where $\lambda_j$ is the density (number per image area) of observed B-type cells;
where $X^i$ is the totality of observed A-type cells identified within the image area;

where $X^j$ is the totality of observed B-type cells identified within the image area within the image area;

where $u \in X^{(i)}$ is a cell being an observed A-type cell;

where r is a stepwise increased radius centered in an observed A-type cell;

wherein t is a function over u, r, and $X^j$ and counts the number of simulated reference B-type cells within a circle of radius r around a simulated reference A-type cell u in the image area;

where "$|u \in X^{(i)}$" means "over all u which are observed A-type cells";

where E is the expected value of t obtained over all u.

8. The image analysis method of claim 4, further comprising:
computing a plurality of initial reference relative distributions in accordance with claim 4;
computing an average reference relative distribution from the plurality of initial reference relative distributions; and
using the average reference relative distribution as the reference relative distribution.

9. The method of claim 1, the obtaining of the reference relative distribution comprising:
receiving a further digital image for each of one or more further tissue samples, each further tissue sample being derived from a tissue of known biomedical state;
analyzing each received further image for identifying the number and location of observed reference A-type cells and observed reference B-type cells having been observed in an area of the received further image;
analyzing the location of the observed reference A-type and the observed reference B-type cells in the area of each further image for obtaining a further observed relative distribution, the further observed relative distribution being indicative of observed distances between the observed reference A-type cells and the observed reference B-type cells having been observed in the area of the further digital image; and
using the observed reference relative distribution as the reference relative distribution.

10. The image analysis method of claim 1, the computing of the proximity score as a difference of the reference relative distribution and the observed relative distribution comprising:
providing a predefined number representing a predefined minimum number of B-type cells;
identifying within the observed relative distribution an observed radius $r_{o\text{-}min}$, wherein the observed radius $r_{o\text{-}min}$ is a radius that—if drawn around each one of the observed A-type cells, would define a circle that comprises on average the predefined number of the observed B-type cells;
identifying within the reference relative distribution a reference radius $r_{r\text{-}min}$, wherein the reference radius $r_{r\text{-}min}$ is a radius that—if drawn around each one of the reference A-type cells, would define a circle that comprises on average the predefined number of the reference B-type cells for providing the reference relative distribution;
computing the proximity score as a function of the observed radius $r_{o\text{-}min}$ and the reference radius $r_{r\text{-}min}$ the function being in particular the difference between the observed radius and the reference radius.

11. The image analysis method of claim 1, further comprising:
graphically representing the observed relative distribution as an observed-distribution curve in a 2D plot whose first dimension represents the radius r (Ro) and whose second dimension represents the number of observed B-type cells associated with said radius; and displaying the 2D plot on a display device of the image analysis system; and/or
graphically representing the reference relative distribution as a reference-distribution curve in a 2D plot whose first dimension represents the radius r (Rs) and whose second dimension represents the number of reference B-type cells associated with said radius; and displaying the 2D plot on a display device of the image analysis system.

12. The image analysis method of claim 1, the A-type cells being tumor cells, the B-type cells being immune cells.

13. The image analysis of claim 1, the tissue sample being a tumor tissue sample and the determination of the biomedical state of the tissue sample comprising determining the infiltration state of the tumor tissue depicted in the area of the received digital image with immune cells.

14. The image analysis of claim 1, further comprising:
graphically representing the combined score as symbol within a score 2D plot, wherein a first dimension of the 2D score plot represents the proximity score and wherein a second dimension of the 2D score plot represents the density of the B-type cells or of the A-type cells; and outputting (214) the 2D score plot on a display of the image analysis system for enabling a human to determine the biomedical state of the tissue sample; and/or
performing the determination of the biomedical state of the tissue sample by the image analysis system by automatically identifying the biomedical state of the tissue sample within a limited set of predefined biomedical states or within a predefined, continuous spectrum of biomedical states and outputting the identified biomedical state as the determined biomedical state.

15. The image analysis method of claim 14, wherein receiving the digital image of the tissue sample comprises receiving a digital image of a tissue sample from each of a plurality of different patients, wherein computing the combined score comprises computing a combined score for each of the patients using the image of the tissue sample from each patient, and wherein the method further comprises:
graphically representing the biomedical state of each patient by a respective, biomedical-state-specific symbol, on a 2D score plot, the position of the symbol of each patient in the plot depending on the B-type cell density and the proximity score computed for the patient.

16. The image analysis method of claim 1, wherein the identified biomedical state is selected from a group comprising:
inflamed, wherein inflamed is indicative of an immunological tissue state in which immune cells have a significantly increased cell density being indicative of a heavy infiltration of the tumor tissue with immune cells in all compartments of the tumor;
excluded, wherein excluded is indicative of an immunological tissue state in which immune cells are present in the tissue sample but are hindered to come into close contact to the tumor cells, whereby the immune cells are concentrated at the invasive margin and/or in the intratumoral stroma but separated from the tumor cells;
desert, wherein desert is indicative of an immunological tissue state in which immune cells in a tumorous tissue region have a cell density that is zero or close to zero.

17. The image analysis method of claim 1, further comprising:
in case the tissue sample is classified into a tumor infiltration type of inflamed, outputting, via a user interface, a treatment recommendation to prescribe a drug acting as checkpoint inhibitor;
in case the tissue sample is classified into a tumor infiltration type of excluded, outputting, via a user interface, a treatment recommendation to prescribe a drug adapted to attract immune cells closer to tumor cells;
in case the tissue sample is classified into a tumor infiltration type of deserted, outputting, via a user interface, a treatment recommendation to prescribe a drug adapted to generically boost the immune system.

18. The image analysis method of claim 1, wherein the density of the reference A-type cells is identical to the density of A-type cells observed in the image area and wherein the density of the reference B-type cells is identical to the density of the B-type cells observed in the image area.

19. A method of determining the efficacy of a drug for treating a particular type of cancer, the method comprising:
receiving a plurality of first digital images, each first image depicting a tissue sample of a respective organism having the particular type of cancer before said organism was treated with the drug;
computing, from an image area of each of the first digital images, a first combined score, the computing, comprising:
(a) analyzing the received image for identifying the number and location of A-type cells and B-type cells observed in the image area, wherein the A-type and the B-type are different cell types;
(b) analyzing the location of the A-type and B-type cells in the area for obtaining an observed relative distribution, the observed relative distribution being indicative of observed distances between the A-type cells and the B-type cells in the area;
(c) obtaining a reference relative distribution, the reference relative distribution being indicative of expected distances between the reference A-type cells and reference B-type cells;
(d) computing a proximity score as a difference of the reference relative distribution and the observed relative distribution; and
(e) computing a combined score, the combined score comprising the proximity score and comprising the density of the A-type cells and/or the density of the B-type cells,
wherein the biomedical state is an immune-cell-infiltration state of a tumor, the A-type cells are tumor cells and the B-type cells are cancer cells, and the first combined score is the combined score of step (e);
receiving a plurality of second digital images, each second image depicting a tissue sample of a respective organism having the particular type of cancer after said organism was treated with the drug;
computing, from an image area of each of the second digital images, a second combined score, the computing comprising performing steps (a)-(e) for each of the received second digital images, wherein the biomedical state is a tumor infiltration state, the A-type cells are tumor cells and the B-type cells are cancer cells, and the second combined score is the combined score of step (d);
displaying a 2D score plot on a display device, wherein each first combined score is represented by a first symbol in the 2D score plot, wherein each second combined score is represented by a second symbol in the 2D score plot, wherein the position of the first and second symbols in the plot depend on the immune cell density observed in the image area of the respective images and on the proximity score computed for the image area of the respective images, wherein first and second symbols representing the same organism are visually linked in the 2D score plot for visualizing any shift in the x and/or y coordinates from any one of the first symbols to its respectively linked second symbol.

20. A non-transitory storage medium comprising computer-interpretable instructions which, when executed by a processor, cause the processor to perform an image analysis method according to claim 1.

21. An image analysis system for determining the biomedical state of a tissue sample, the system comprising a processor and computer-interpretable instructions configured to cause the processor executing the instructions to perform a method comprising:
receiving a digital image of the tissue sample;
analyzing the received image for identifying the number and location of A-type cells and B-type cells observed in an area of the received image, wherein the A-type and the B-type are different cell types;
analyzing the location of the A-type and B-type cells in the area for obtaining an observed relative distribution, the observed relative distribution being indicative of observed distances between the A-type cells and the B-type cells in the area;
obtaining a reference relative distribution, the reference relative distribution being indicative of expected distances between the reference A-type cells and reference B-type cells, wherein the expected distances are the distances that are expected assuming that the A-type cells and/or the B-type cells are distributed in the image area in accordance with a particular predefined mathematical distribution;
computing a proximity score as a difference of the reference relative distribution and the observed relative distribution;
computing a combined score, the combined score comprising the proximity score and comprising the density of the A-type cells and/or the density of the B-type cells;
using the combined score for determining the biomedical state of the tissue sample and/or outputting the combined score to a user for enabling the user to determine the biomedical state of the tissue sample.

* * * * *